(12) United States Patent
Arbetman et al.

(10) Patent No.: US 8,007,780 B2
(45) Date of Patent: Aug. 30, 2011

(54) AAV VECTORS FOR GENE DELIVERY TO THE LUNG

(75) Inventors: Alejandra E. Arbetman, San Francisco, CA (US); Michael A. Lochrie, Hayward, CA (US)

(73) Assignee: Genzyme Corporation, Framingham, MA (US)

( * ) Notice: Subject to any disclaimer, the term of this patent is extended or adjusted under 35 U.S.C. 154(b) by 0 days.

(21) Appl. No.: 12/154,531

(22) Filed: May 23, 2008

(65) Prior Publication Data

US 2008/0292595 A1    Nov. 27, 2008

Related U.S. Application Data

(62) Division of application No. 11/143,866, filed on Jun. 2, 2005, now Pat. No. 7,427,396.

(60) Provisional application No. 60/576,506, filed on Jun. 3, 2004, provisional application No. 60/582,037, filed on Jun. 21, 2004.

(51) Int. Cl.
*A01N 65/00* (2009.01)
*A01N 63/00* (2006.01)
*A61K 48/00* (2006.01)

(52) U.S. Cl. ............ 424/93.2; 424/93.1; 514/44 R; 435/320.1

(58) Field of Classification Search .......... 424/93.2, 424/93.1; 514/44 R; 435/320
See application file for complete search history.

(56) References Cited

U.S. PATENT DOCUMENTS

| | | | |
|---|---|---|---|
| 5,139,941 A | 8/1992 | Muzyczka et al. | |
| 6,001,650 A | 12/1999 | Colosi | |
| 6,004,797 A | 12/1999 | Colosi | |
| 6,156,303 A | 12/2000 | Russell et al. | |
| 6,376,237 B1 | 4/2002 | Colosi | |
| 2007/0072282 A1* | 3/2007 | Chiorini et al. | 435/235.1 |

OTHER PUBLICATIONS

Driskell and Engelhardt, An Rev Physiol 65:585-612, 2003.*
Gautam et al. Am J Respir Med 1(1):35-46, 2002.*
Auricchio, et al., "Noninvasive Gene Transfer to the Lung for Systematic Delivery of Therapeutic Proteins," *J Clin Invest* 110(4):499-504 (2002).
Balls, et al., "Transduction of Well-Differentiated Airway Epithelium by Recombinant Adeno-Associated Virus is Limited by Vector Entry," *J Virol* 73(7):6085-6088 (1999).
Beck, et al., "Repeated Delivery of Adeno-Associated Virus Vectors to the Rabbit Airway," *J Virol* 73(11):9446-9455 (1999).
(Bovine or Cow or Cattle) VP1 Entrez Sequence Search, 5 Pages, printout dated Jun. 3, 2006.
(Caprine of Goat) AAV Entrez Sequence Search, 3 Pages, printout dated Jun. 3, 2006.

Chirioni, et al., "Cloning and Characterization of Adeno-Associated Virus Type 5," *J Virol* 73(2):1309-1319 (1999).
De, et al., "Intrapleural Administration of a Serotype 5 Adeno-Associated Virus Coding for a 1-Antitrypsin Mediates Persistant, High Lung Serum Levels of a 1-Antitrypsin," *Mol Ther* 10(6):1003-1010 (2004).
Fischer, et al., "Succesful Transgene Expression with Serial Doses of Aerosolized rAAV2 Vectors in Rhesus Macaques," *Mol Ther* 8(6):918-926 (2003).
Flotte, et al., "Phase I Trial of Intranasal and Endobronchial Administration of a Recombinant Adeno-Associated Virus Serotype 2 (rAAV2)-CFTR Vector in Adult Cystic Fibrosis Patients: A Two-Part Clinical Study," *Hum Gene Ther* 14(11):1079-1088 (2003).
Flotte, et al., "Recent Developments in Recombinant AAV-Mediated Gene Therapy for Lung Diseases," *Curr Gene Therapy* 5:361-366 (2005).
Gao, et al., "Novel Adeno-Associated Viruses from Rhesus Monkeys as Vectors for Human Gene Therapy," *PNAS* 99(18):11854-11859 (2002).
Goncz, et al., "Expression of DeltaF508 CFTR in Normal Mouse Lung After Site-Specific Modification of CFTR Sequences by SFHR," *Gene Ther* 8(12):961-965, 2001.
Grimm, et al., "Preclinical In Vivo Evaluation of Pseudotyped Adeno-Associated Virus Vectors for Liver Gene Therapy," *Blood* 102(7):2412-2419 (2003).
Halbert, et al., "Repeat Transduction in the Mouse Lung by Using Adeno-Associated Virus Vectors with Different Serotypes," J Virol 74(3):1524-1532 (2000).
Halbert, et al., "Adeno-Associated Virus Type 6 (AAV6) Vectors Mediate Efficient Transduction of Airway Epithelial Cells in Mouse Lungs Compared too . . . ," J Virol 75(14):6615-6624 (2001).
Heid, et al., "Real time Quantitative PCR," *Genome Res* 6(10):986-994 (1996).
Holfland, et al., "In Vivo Gene Transfer by Intraveneous Administration of Stable Cationic Lipid/DNA Complex," Pharm Res 14(6):742-749 (1997).
Matsushita, et al., "Adeno-Associated Virus Vectors can be Efficiently Produced Without Helper Virus," *Gene Ther* 5(7):938-945 (1998).
Miao, et al., "Inclusion of the Hepatic Locus Control Region, an Intron, and Untranslated Region Increases ans Stabilizes Hepatic Factor IX Gene Expression In Vivo but Not In Vitro," *Mol Ther* 1(6):522-532 (2000).
Miao, et al., "High-Level Factor VIII Gene Expression In Vivo Achieved by NonViral Liver-Specific Gene Therapy Vectors," *Hum Gene Ther* 14(14):1297-1305 (2003).
Rutledge, et al., "Infectious Clones and Vectors Derived from Adeno-Associated Virus (AAV) Serotypes Other the AAV Types 2," *J Virol* 72(1):309-319 (1998).
Schmidt, et al., "Cloning and Characterization of a Bovine Adeno-Associated Virus," *J Virol* 78(12):6509-6516 (2004).
Sommer, et al., "Quantification of Adeno-Associated Virus Particles and Empty Capsids by Optical Density Measurement," *Mol Ther* 7(1):122-128 (2003).

(Continued)

*Primary Examiner* — Deborah Crouch
*Assistant Examiner* — Marcia S Noble
(74) *Attorney, Agent, or Firm* — Robins & Pasternak LLP

(57) ABSTRACT

Methods of making and using recombinant AAV vectors and virions for gene delivery to the lung are described. The recombinant AAV virions are derived from caprine AAV and bovine AAV, both of which display tropism for lung tissue.

7 Claims, 9 Drawing Sheets

OTHER PUBLICATIONS

Walter, et al., "Successful Expression of Human Factor IX Following Repeat Administration of Adenoviral Vector in Mice," *PNAS* 93(7):3056-3061 (1996).

Wilson, et al., "Gene Therapy for Cystic Fibrosis: Challenges and Future Directions," *J Clin Invest* 96(6):2547-2554 (1995).

* cited by examiner

|   |   |   |
|---|---|---|
| Primate AAV type 5 | VP1<br>atgtcttttgttgatcaccctccagattggttggaagaagttgg | 2250 |
| Caprine AAV | ............................................ |   |
| Primate AAV type 5 | tgaaggtcttcgcgagttttggggccttgaagcgggcccaccgaaaccaa | 2300 |
| Caprine AAV | .................................................. |   |
| Primate AAV type 5 | aacccaatcagcagcatcaagatcaagcccgtggtcttgtgctgcctggt | 2350 |
| Caprine AAV | .................................................. |   |
| Primate AAV type 5 | tataactatctcggacccggaaacggtctcgatcgaggagagcctgtcaa | 2400 |
| Caprine AAV | .................................................. |   |
| Primate AAV type 5 | cagggcagacgaggtcgcgcgagagcacgacatctcgtacaacgagcagc | 2450 |
| Caprine AAV | .................................................. |   |
| Primate AAV type 5 | ttgaggcgggagacaaccccctacctcaagtacaaccacgcggacgccgag | 2500 |
| Caprine AAV | .................................................. |   |
| Primate AAV type 5 | tttcaggagaagctcgccgacgacacatccttcggggggaaacctcggaaa | 2550 |
| Caprine AAV | .................................................. |   |
| Primate AAV type 5 | ggcagtctttcaggccaagaaagggttctcgaacctttggcctggttg | 2600 |
| Caprine AAV | .................................................. |   |
| Primate AAV type 5 | aagagggtgctaagacggcccctaccggaaagcggatagacgaccactt | 2650 |
| Caprine AAV | .................................................. |   |
| Primate AAV type 5 | ccaaaaagaaagaaggctcggaccgaagaggactccaagccttccacctc | 2700 |
| Caprine AAV | .................................................. |   |
| Primate AAV type 5 | gtcagacgccgaagctggaccccagcggatcccagcagctgcaaatcccag | 2750 |
| Caprine AAV | .................................................. |   |
| Primate AAV type 5 | cccaaccagcctcaagtttgggagctgatacaatgtctgcgggaggtggc | 2800 |
| Caprine AAV | .a................................................ |   |
| Primate AAV type 5 | ggccattgggcgacaataaccaaggtgccgatggagtgggcaatgcctc | 2850 |
| Caprine AAV | ..............................................--- |   |
| Primate AAV type 5 | gggagattggcattgcgattccacgtggatgggggacagagtcgtcacca | 2900 |
| Caprine AAV | .................................................. |   |
| Primate AAV type 5 | agtccacccgaacctgggtgctgcccagctacaacaaccaccagtaccga | 2950 |
| Caprine AAV | ..........c....................................... |   |
| Primate AAV type 5 | gagatcaaaagcggctccgtcgacggaagcaacgccaacgcctactttgg | 3000 |
| Caprine AAV | .................................................. |   |
| Primate AAV type 5 | atacagcaccccctgggggtactttgactttaaccgcttccacagccact | 3050 |
| Caprine AAV | .................................................. |   |
| Primate AAV type 5 | ggagcccccgagactggcaaagactcatcaacaactactggggcttcaga | 3100 |
| Caprine AAV | ...............................t.................. |   |
| Primate AAV type 5 | cccccggtccctcagagtcaaaatcttcaacattcaagtcaaagaggtcac | 3150 |
| Caprine AAV | ........t.....................c.................. |   |
| Primate AAV type 5 | ggtgcaggactccaccaccaccatcgccaacaacctcacctccaccgtcc | 3200 |
| Caprine AAV | .................................................. |   |
| Primate AAV type 5 | aagtgtttacggacgacgactaccagctgccctacgtcgtcggcaacggg | 3250 |
| Caprine AAV | ..........................a..c..g................ |   |
| Primate AAV type 5 | accgagggatgcctgccggccttccctccgcaggtctttacgctgccgca | 3300 |
| Caprine AAV | ............................c..................... |   |

Fig. 2A

| | | |
|---|---|---|
| Primate AAV type 5<br>Caprine AAV | gtacggttacgcgacgctgaaccgcgacaacacagaaaatcccaccgaga<br>......c.............a......gg...c..c..g..a...c | 3350 |
| Primate AAV type 5<br>Caprine AAV | ggagcagcttcttctgcctagagtactttcccagcaagatgctgagaacg<br>..............t.............................g... | 3400 |
| Primate AAV type 5<br>Caprine AAV | ggcaacaactttgagtttacctacaactttgaggaggtgcccttccactc<br>......................g......a.................g | 3450 |
| Primate AAV type 5<br>Caprine AAV | cagcttcgctcccagtcagaacctgttcaagctggccaacccgctggtgg<br>..........c...g..c........c..t.................. | 3500 |
| Primate AAV type 5<br>Caprine AAV | accagtacttgtaccgcttcgtgagcacaaataacactggcggagtccag<br>.........c....................ctcggc...g....cca..... | 3550 |
| Primate AAV type 5<br>Caprine AAV | ttcaacaagaacctggccgggagatacgccaacacctacaaaaactggtt<br>...c.a..........g..c............................ | 3600 |
| Primate AAV type 5<br>Caprine AAV | cccggggcccatgggccgaacccagggctggaacctgggctccggggtca<br>.................................ac.a....t...  .. | 3650 |
| Primate AAV type 5<br>Caprine AAV | accgcgc---cagtgtcagcgccttcgccacgacc------aataggatg<br>g.a...a.caa...a.......t.aa.aa.tttt..gtctca..cc..... | 3691 |
| Primate AAV type 5<br>Caprine AAV | gagctcgagggcgcgagttaccaggtgcccccgcagccgaacggcatgac<br>a.c..g.....g..c..c......a...aa...c.....c.....g..... | 3741 |
| Primate AAV type 5<br>Caprine AAV | caacaacctccagggcagcaacacctatgccctggagaacactatgatct<br>a....cg.....a.........cg...c..g.....a.....c....... | 3791 |
| Primate AAV type 5<br>Caprine AAV | tcaacagccagccggcgaacccgggcaccaccgccacgtacctcgagggc<br>.....gct..aaac..c.cg.....a..t...t.ggt.....ca....a. | 3841 |
| Primate AAV type 5<br>Caprine AAV | aacatgctcatcaccagcgagagcgagacgcagccggtgaaccgcgtggc<br>..tc.a..gc.g................t.....c..c.....g..... | 3891 |
| Primate AAV type 5<br>Caprine AAV | gtacaacgtcggcgggcagatggccaccaacaaccagagctccaccactg<br>t......acg.....t...............gc.....a.g.......g. | 3941 |
| Primate AAV type 5<br>Caprine AAV | cccccgcgaccggcacgtacaacctccaggaaatcgtgcccggcagcgtg<br>.t...a..gt...g...c.............g.gc.t..t........a | 3991 |
| Primate AAV type 5<br>Caprine AAV | tggatggagagggacgtgtacctccaaggacccatctgggccaagatccc<br>.................................................. | 4041 |
| Primate AAV type 5<br>Caprine AAV | agagacgggggcgcactttcacccctctccggccatgggcggattcggac<br>.................................................. | 4091 |
| Primate AAV type 5<br>Caprine AAV | tcaaacacccaccgcccatgatgctcatcaagaacacgcctgtgcccgga<br>..........g.................a..........g........c | 4141 |
| Primate AAV type 5<br>Caprine AAV | aatatcaccagcttctcggacgtgcccgtcagcagcttcatcacccagta<br>..c.............................................. | 4191 |
| Primate AAV type 5<br>Caprine AAV | cagcaccgggcaggtcaccgtggagatggagtgggagctcaagaaggaaa<br>.............................a..........a....... | 4241 |
| Primate AAV type 5<br>Caprine AAV | actccaagaggtggaacccagagatccagtacacaaacaactacaacgac<br>.........................................c......... | 4291 |
| Primate AAV type 5<br>Caprine AAV | ccccagtttgtggactttgccccggacagcaccggggaatacagaaccac<br>....................t..a...g..t....c............. | 4341 |
| Primate AAV type 5<br>Caprine AAV | cagacctatcggaacccgataccttacccgaccccctt (Seq ID No:1)<br>....g.c..........c............ (Seq ID No:3) | 4378 |

Fig. 2B

```
Primate AAV type 5 VP1  MSFVDHPPDWLEEVGEGLREFLGLEAGPPKPKPNQQHQDQARGLVLPGYNYLGPGNGLDR  60
Caprine AAV VP1         ............................................................  60

Primate AAV type 5 VP1  GEPVNRADEVAREHDISYNEQLEAGDNPYLKYNHADAEFQEKLADDTSFGGNLGKAVFQA  120
Caprine AAV VP1         ............................................................  120

Primate AAV type 5 VP1  KKRVLEPFGLVEEGAKTAPTGKRIDDHFPKRKKARTEEDSKPSTSSDAEAGPSGSQQLQI  180
Caprine AAV VP1         ............................................................  180

Primate AAV type 5 VP1  PAQPASSLGADTMSAGGGGPLGDNNQGADGVGNASGDWHCDSTWMGDRVVTKSTRTWVLP  240
Caprine AAV VP1         ............................................................  240

Primate AAV type 5 VP1  SYNNHQYREIKSGSVDGSNANAYFGYSTPWGYFDFNRFHSHWSPRDWQRLINNYWGFRPR  300
Caprine AAV VP1         ............................................................  300

Primate AAV type 5 VP1  SLRVKIFNIQVKEVTVQDSTTTIANNLTSTVQVFTDDDYQLPYVVGNGTEGCLPAFPPQV  360
Caprine AAV VP1         ............................................................  360

Primate AAV type 5 VP1  FTLPQYGYATLNRDNTENPTERSSFFCLEYFPSKMLRTGNNFEFTYNFEEVPFHSSFAPS  420
Caprine AAV VP1         ..............GD........................S.......C.....  420

Primate AAV type 5 VP1  QNLFKLANPLVDQYLYRFVSTNNTGGVQFNKNLAGRYANTYKNWFPGPMGRTQGWNLGSG  480
Caprine AAV VP1         ....................SA..AI..Q.........................IS..  480

Primate AAV type 5 VP1  --VNRASVSAFATTNRMELEGASYQVEPQPNGMTNNLQGSNIYALENTMIFNSQPANPGT  538
Caprine AAV VP1         SST..V..NN.SVS...N........N........T....R..........A.N.T...  540

Primate AAV type 5 VP1  TATYLEGNMLITSESETQPVNRVAYNVGGQMATNNQSTTAPATGTYNLQEIVPGSVWME  598
Caprine AAV VP1         .SV.P.D.L.L.............T.......A.NA....TV.......VL.......  600

Primate AAV type 5 VP1  RDVYLQGPIWAKIPETGAHFHPSPAMGGFGLKHPPPMMLIKNTPVPGNITSFSDVPVSSF  658
Caprine AAV VP1         ............................................................  660

Primate AAV type 5 VP1  ITQYSTGQVTVEMEWELKKENSKRWNPEIQYTNNYNDPQFVDFAPDSTGEYRTTRPIGTR  718
Caprine AAV VP1         ..............................................GS.......A....  720

Primate AAV type 5 VP1  YLTRPL 724 (Seq ID No:2)
Caprine AAV VP1         ...... 726 (Seq ID No:4)
```

FIG. 3

```
                  1                                                50
Bovine AAV:MSFVDHPPDWLESIGDGFREFLGLEAGPPKPKANQQKQDNARGLVLPGYK
Schmidt et al.:..................................................
                 51                                               100
Bovine AAV:YLGPGNGLDKGDPVNFADEVAREHDLSYQKQLEAGDNPYLKYNHADAEFQ
Schmidt et al.:..................................................
                101                                               150
Bovine AAV:EKLASDTSFGGNLGKAVFQAKKRILEPLGLVETPDKTAPAAKKRPLEQSP
Schmidt et al.:..................................................
                151                                               200
Bovine AAV:QEPDSSSGVGKKGKQPARKRLNFDDEPGAGDGPPPEGPSSGAMSTETEMR
Schmidt et al.:..................................................
                201                                               250
Bovine AAV:AAAGGNGGDAGQGAEGVGNASGDWHCDSTWSESHVTTTSTRTWVLPTYNN
Schmidt et al.:..................................................
                251                                               300
Bovine AAV:HLYLRLGSSNASDTFNGFSTPWGYFDFNRFHCHFSPRDWQRLINNHWGLR
Schmidt et al.:..................................................
                301                                               350
Bovine AAV:PKSMQVRIFNIQVKEVTTSNGETTVSNNLTSTVHIFADSTYELPYVMDAG
Schmidt et al.:.............................Q....................
  Accessibility:                              B
                351                                               400
Bovine AAV:QEGSLPPFPNDVFMVPQYGYCGLVTGGSSQNQTDRNAFYCLEYFPSQMLR
Schmidt et al.: .................................................
                401                                               450
Bovine AAV:TGNNFEMVYKFENVPFHSMYAHSQSLDRLMNPLLDQYLWELQSTTSGGTL
Schmidt et al.: .................................................
                451                                               500
Bovine AAV:NQGNSATNFAKLTNKNFSGYRKNWLPGPMMKQQRFSKTASQNYKIPQGGN
Schmidt et al.:............KT...............................R.
  Accessibility:            OO                                   O
Surface Feature:            PP                                   S
                501                                               550
Bovine AAV:NSLLHYETRTTLDRRWSNFAPGTAMATAANDATDFSQAQLIFAGPNITGN
Schmidt et al.:.............G....................................
  Accessibility:             O
Surface Feature:             P
                551                                               600
Bovine AAV:TTTDANNLMFTSEDELRATNPRDTDLFGHLATNQQNATTVPTVDDVDGVG
Schmidt et al.: .................................................
                601                                               650
Bovine AAV:VYPGMVWQDRDIYYQGPIWAKIPHTDGHFHPSPLIGGFGLKSPPPQIFIK
Schmidt et al.: .................................................
                651                                               700
Bovine AAV:NTPVPANPATTFSPARINSFITQYSTGQVAVKIEWEIQKERSKRWNPEVQ
Schmidt et al.: .................................................
                701                            736
Bovine AAV:FTSNYGAQDSLLWAPDNAGAYKEPRAIGSRYLTNHL (Seq ID No:5)
Schmidt et al.: ..................................  (Seq ID No:6)
```

Fig. 5

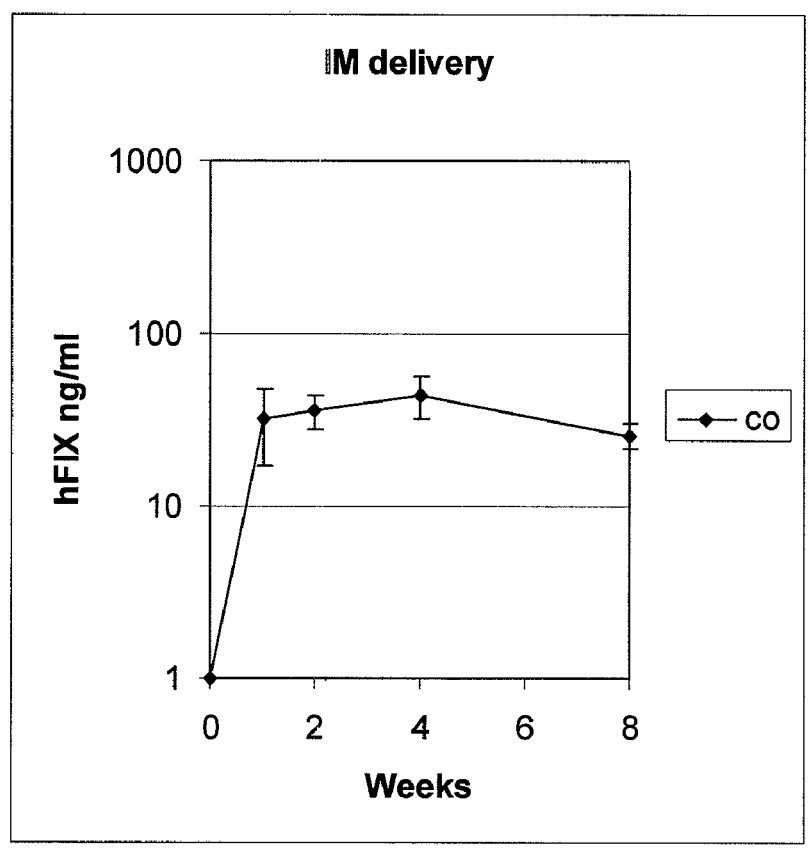
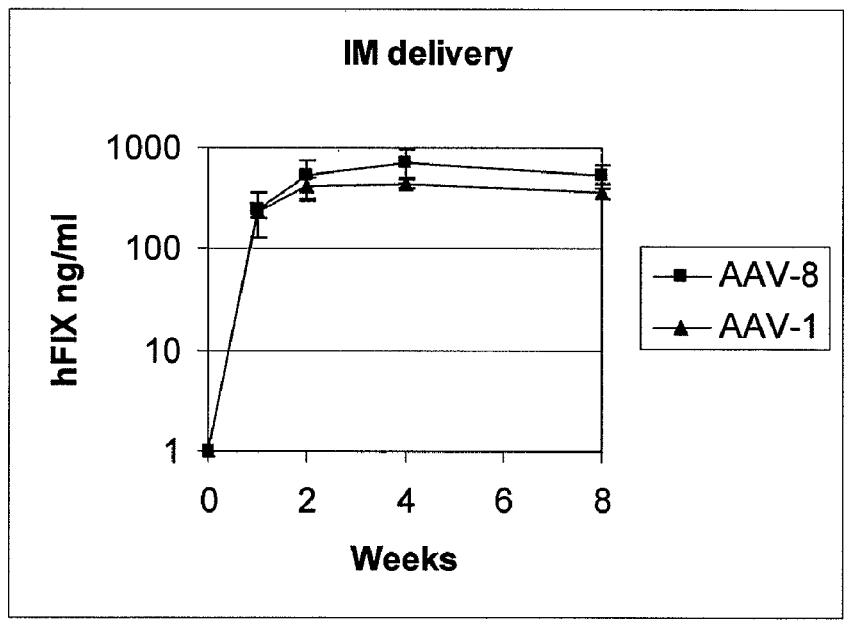
Fig. 6

SEQUENCE LISTING

<160> NUMBER OF SEQ ID NOS: 14

<210> SEQ ID NO 1
<211> LENGTH: 2172
<212> TYPE: DNA
<213> ORGANISM: Artificial
<220> FEATURE:
<223> OTHER INFORMATION: nucleotide sequence encoding the AAV VP1
      protein from a primate AAV-5

<400> SEQUENCE: 1

```
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccgaaacgg tctcgatcga      180 ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc tttttggcctg gttgaagagg gtgctaagac ggcccctacc     420
ggaaagcgga tagacgacca ctttccaaaa agaaagaagg ctcggaccga agaggactcc     480
aagccttcca cctcgtcaga cgccgaagct ggacccagcg gatcccagca gctgcaaatc     540
ccagcccaac cagcctcaag tttgggagct gatacaatgt ctgcgggagg tggcggccca     600
ttgggcgaca ataaccaagg tgccgatgga gtgggcaatg cctcgggaga ttggcattgc     660
gattccacgt ggatggggga cagagtcgtc accaagtcca cccgaacctg ggtgctgccc     720
agctacaaca accaccagta ccgagagatc aaaagcggct ccgtcgacgg aagcaacgcc     780
aacgcctact ttggatacag caccccctgg gggtactttg actttaaccg cttccacagc     840
```

```
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgccccgca gccgaacggc atgaccaaca cctccagggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggcgca ctttcaccccc   1860
tctccggcca tgggcggatt cggactcaaa cacccaccgc catgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gttttgtggac   2100
tttgccccgg acagcaccgg ggaatacaga accaccagac ctatcggaac ccgataccttt   2160
acccgacccc tt                                                       2172
```

<210> SEQ ID NO 2
<211> LENGTH: 724
<212> TYPE: PRT
<213> ORGANISM: Artificial
<220> FEATURE:
<223> OTHER INFORMATION: amino acid sequence of VP1 from a primate AAV-5

<400> SEQUENCE: 2

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125
```

```
Gly Leu Val Glu Glu Gly Ala Lys Thr Ala Pro Thr Gly Lys Arg Ile
130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560
```

```
Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 3
<211> LENGTH: 2181
<212> TYPE: DNA
<213> ORGANISM: Artificial
<220> FEATURE:
<223> OTHER INFORMATION: nucleotide sequence encoding the AAV VP1
      protein from a caprine AAV

<400> SEQUENCE: 3
atgtcttttg ttgatcaccc tccagattgg ttggaagaag ttggtgaagg tcttcgcgag    60
tttttgggcc ttgaagcggg cccaccgaaa ccaaaaccca atcagcagca tcaagatcaa   120
gcccgtggtc ttgtgctgcc tggttataac tatctcggac ccggaaacgg tctcgatcga   180
ggagagcctg tcaacagggc agacgaggtc gcgcgagagc acgacatctc gtacaacgag   240
cagcttgagg cgggagacaa ccctacctc aagtacaacc acgcggacgc cgagtttcag   300
gagaagctcg ccgacgacac atccttcggg ggaaacctcg gaaaggcagt ctttcaggcc   360
aagaaaaggg ttctcgaacc ttttggcctg gttgagagg gtgctaagac ggcccctacc   420
ggaaagcgga tagacgacca ctttccaaaa agaaagaagg ctcggaccga gaggactcc   480 aagccttcca cctcgtcaga cgccgaagct ggacccagcg atcccagca gctgcaaatc   540 ccagcacaac cagcctcaag tttgggagct gatacaatgt ctgcggagg tggcggccca   600 ttgggcgaca taaccaagg tgccgatgga gtggcaatg cctcgggaga ttggcattgc   660
gattccacgt ggatggggga cagagtcgtc accaagtcca cccgcacctg ggtgctgccc   720
agctacaaca accaccagta ccgagagatc aaaagcggct ccgtcgacgg aagcaacgcc   780
aacgcctact ttggatacag cacccctgg gggtactttg actttaaccg cttccacagc   840
cactggagcc cccgagactg gcaaagactc atcaacaact attggggctt cagaccccgg   900
tctctcagag tcaaaatctt caacatccaa gtcaagagg tcacggtgca ggactccacc   960
accaccatcg ccaacaacct cacctccacc gtccaagtgt ttacggacga cgactaccaa  1020
ctcccgtacg tcgtcggcaa cgggaccgag ggatgcctgc cggccttccc cccgcaggtc  1080
```

```
tttacgctgc cgcagtacgg ctacgcgacg ctgaaccgag acaacggaga caacccgaca    1140
gagcggagca gcttcttttg cctagagtac tttcccagca agatgctgag gacgggcaac    1200
aactttgagt ttacctacag ctttgaagag gtgcccttcc actgcagctt cgccccgagc    1260
cagaacctct ttaagctggc caacccgctg gtggaccagt acctgtaccg cttcgtgagc    1320
acctcggcca cgggcgccat ccagttccaa aagaacctgg cgggcagata cgccaacacc    1380
tacaaaaact ggttcccggg gcccatgggc cgaacccagg gctggaacac gagctctggg    1440
gtcagcagca ccaacagagt cagcgtcaac aacttttccg tctcaaaccg gatgaacctg    1500
gagggggcca gctaccaagt gaaccccag cccaacggga tgacaaacac gctccaaggc    1560
agcaaccgct acgcgctgga aaacaccatg atcttcaacg ctcaaaacgc cacgccggga    1620
actacctcgg tgtacccaga ggacaatcta ctgctgacca gcgagagcga gactcagccc    1680
gtcaaccggg tggcttacaa cacgggcggt cagatggcca ccaacgccca gaacgccacc    1740
acggctccca cggtcgggac ctacaacctc caggaagtgc ttcctggcag cgtatggatg    1800
gagagggacg tgtacctcca aggacccatc tgggccaaga tcccagagac ggggggcgcac    1860 tttcacccct ctccggccat gggcggattc ggactcaaac accgccgcc catgatgctc    1920 atcaaaaaca cgccggtgcc cggcaacatc accagcttct cggacgtgcc cgtcagcagc    1980
ttcatcaccc cagtacagcac cgggcaggtc accgtggaga tggaatggga gctcaaaaag    2040
gaaaactcca agaggtggaa cccagagatc cagtacacca acaactacaa cgacccccag    2100
tttgtggact tgctccaga cggctccggc gaatacagaa ccaccagagc catcggaacc    2160 cgataccttca cccgaccct t                                              2181
```

<210> SEQ ID NO 4
<211> LENGTH: 726
<212> TYPE: PRT
<213> ORGANISM: Artificial
<220> FEATURE:
<223> OTHER INFORMATION: amino acid sequence of VP1 from a caprine AAV

<400> SEQUENCE: 4

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175
```

```
Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Gln Gly Ala
            195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Gly Asp Asn Pro Thr Glu Arg Ser Ser
            370                 375                 380

Phe Phe Cys Leu Glu Tyr Phe Pro Ser Lys Met Leu Arg Thr Gly Asn
385                 390                 395                 400

Asn Phe Glu Phe Thr Tyr Ser Phe Glu Glu Val Pro Phe His Cys Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Ser Ala Thr Gly Ala Ile Gln
            435                 440                 445

Phe Gln Lys Asn Leu Ala Gly Arg Tyr Ala Asn Thr Tyr Lys Asn Trp
            450                 455                 460

Phe Pro Gly Pro Met Gly Arg Thr Gln Gly Trp Asn Thr Ser Ser Gly
465                 470                 475                 480

Ser Ser Thr Asn Arg Val Ser Val Asn Asn Phe Ser Val Ser Asn Arg
                485                 490                 495

Met Asn Leu Glu Gly Ala Ser Tyr Gln Val Asn Pro Gln Pro Asn Gly
            500                 505                 510

Met Thr Asn Thr Leu Gln Gly Ser Asn Arg Tyr Ala Leu Glu Asn Thr
            515                 520                 525

Met Ile Phe Asn Ala Gln Asn Ala Thr Pro Gly Thr Thr Ser Val Tyr
            530                 535                 540

Pro Glu Asp Asn Leu Leu Leu Thr Ser Glu Ser Glu Thr Gln Pro Val
545                 550                 555                 560

Asn Arg Val Ala Tyr Asn Thr Gly Gly Gln Met Ala Thr Asn Ala Gln
                565                 570                 575

Asn Ala Thr Thr Ala Pro Thr Val Gly Thr Tyr Asn Leu Gln Glu Val
            580                 585                 590

Leu Pro Gly Ser Val Trp Met Glu Arg Asp Val Tyr Leu Gln Gly Pro
```

```
                595                 600                 605
Ile Trp Ala Lys Ile Pro Glu Thr Gly Ala His Phe His Pro Ser Pro
610                 615                 620

Ala Met Gly Gly Phe Gly Leu Lys His Pro Pro Met Met Leu Ile
625                 630                 635                 640

Lys Asn Thr Pro Val Pro Gly Asn Ile Thr Ser Phe Ser Asp Val Pro
                645                 650                 655

Val Ser Ser Phe Ile Thr Gln Tyr Ser Thr Gly Gln Val Thr Val Glu
                660                 665                 670

Met Glu Trp Glu Leu Lys Lys Glu Asn Ser Lys Arg Trp Asn Pro Glu
            675                 680                 685

Ile Gln Tyr Thr Asn Asn Tyr Asn Asp Pro Gln Phe Val Asp Phe Ala
            690                 695                 700

Pro Asp Gly Ser Gly Glu Tyr Arg Thr Thr Arg Ala Ile Gly Thr Arg
705                 710                 715                 720

Tyr Leu Thr Arg Pro Leu
                725

<210> SEQ ID NO 5
<211> LENGTH: 736
<212> TYPE: PRT
<213> ORGANISM: Artificial
<220> FEATURE:
<223> OTHER INFORMATION: amino acid sequence of the capsid proteins
      (VP1) of bovine AAV disclosed herein

<400> SEQUENCE: 5

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Lys Lys Arg
    130                 135                 140

Pro Leu Glu Gln Ser Pro Gln Glu Pro Asp Ser Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Gly Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
```

```
            225                 230                 235                 240
Arg Thr Trp Val Leu Pro Thr Tyr Asn Asn His Leu Tyr Leu Arg Leu
                    245                 250                 255

Gly Ser Ser Asn Ala Ser Asp Thr Phe Asn Gly Phe Ser Thr Pro Trp
                260                 265                 270

Gly Tyr Phe Asp Phe Asn Arg Phe His Cys His Phe Ser Pro Arg Asp
            275                 280                 285

Trp Gln Arg Leu Ile Asn His Trp Gly Leu Arg Pro Lys Ser Met
        290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val His Ile Phe
                    325                 330                 335

Ala Asp Ser Thr Tyr Glu Leu Pro Tyr Val Met Asp Ala Gly Gln Glu
                340                 345                 350

Gly Ser Leu Pro Pro Phe Pro Asn Asp Val Phe Met Val Pro Gln Tyr
            355                 360                 365

Gly Tyr Cys Gly Leu Val Thr Gly Gly Ser Ser Gln Asn Gln Thr Asp
        370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                    405                 410                 415

His Ser Met Tyr Ala His Ser Gln Ser Leu Asp Arg Leu Met Asn Pro
                420                 425                 430

Leu Leu Asp Gln Tyr Leu Trp Glu Leu Gln Ser Thr Thr Ser Gly Gly
            435                 440                 445

Thr Leu Asn Gln Gly Asn Ser Ala Thr Asn Phe Ala Lys Leu Thr Asn
        450                 455                 460

Lys Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
                    485                 490                 495

Gln Gly Gly Asn Asn Ser Leu Leu His Tyr Glu Thr Arg Thr Thr Leu
                500                 505                 510

Asp Arg Arg Trp Ser Asn Phe Ala Pro Gly Thr Ala Met Ala Thr Ala
            515                 520                 525

Ala Asn Asp Ala Thr Asp Phe Ser Gln Ala Gln Leu Ile Phe Ala Gly
        530                 535                 540

Pro Asn Ile Thr Gly Asn Thr Thr Asp Ala Asn Asn Leu Met Phe
545                 550                 555                 560

Thr Ser Glu Asp Glu Leu Arg Ala Thr Asn Pro Arg Asp Thr Asp Leu
                    565                 570                 575

Phe Gly His Leu Ala Thr Asn Gln Gln Asn Ala Thr Thr Val Pro Thr
                580                 585                 590

Val Asp Asp Val Asp Gly Val Gly Val Tyr Pro Gly Met Val Trp Gln
            595                 600                 605

Asp Arg Asp Ile Tyr Tyr Gln Gly Pro Ile Trp Ala Lys Ile Pro His
        610                 615                 620

Thr Asp Gly His Phe His Pro Ser Pro Leu Ile Gly Phe Gly Leu
625                 630                 635                 640

Lys Ser Pro Pro Pro Gln Ile Phe Ile Lys Asn Thr Pro Val Pro Ala
                    645                 650                 655
```

```
Asn Pro Ala Thr Thr Phe Ser Pro Ala Arg Ile Asn Ser Phe Ile Thr
                660                 665                 670

Gln Tyr Ser Thr Gly Gln Val Ala Val Lys Ile Glu Trp Glu Ile Gln
            675                 680                 685

Lys Glu Arg Ser Lys Arg Trp Asn Pro Glu Val Gln Phe Thr Ser Asn
        690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 6
<211> LENGTH: 736
<212> TYPE: PRT
<213> ORGANISM: Artificial
<220> FEATURE:
<223> OTHER INFORMATION: amino acid sequence of the capsid proteins
      (VP1) of Schmidt bovine AAV

<400> SEQUENCE: 6

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Ala Lys Lys Arg
    130                 135                 140

Pro Leu Glu Gln Ser Pro Gln Glu Pro Asp Ser Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Ala Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285
```

-continued

```
Trp Gln Arg Leu Ile Asn Asn His Trp Gly Leu Arg Pro Lys Ser Met
    290                 295                 300
Gln Val Arg Ile Phe Asn Ile Gln Val Lys Glu Val Thr Thr Ser Asn
305                 310                 315                 320
Gly Glu Thr Thr Val Ser Asn Asn Leu Thr Ser Thr Val Gln Ile Phe
                325                 330                 335
Ala Asp Ser Thr Tyr Glu Leu Pro Tyr Val Met Asp Ala Gly Gln Glu
            340                 345                 350
Gly Ser Leu Pro Pro Phe Pro Asn Asp Val Phe Met Val Pro Gln Tyr
        355                 360                 365
Gly Tyr Cys Gly Leu Val Thr Gly Gly Ser Ser Gln Asn Gln Thr Asp
    370                 375                 380
Arg Asn Ala Phe Tyr Cys Leu Glu Tyr Phe Pro Ser Gln Met Leu Arg
385                 390                 395                 400
Thr Gly Asn Asn Phe Glu Met Val Tyr Lys Phe Glu Asn Val Pro Phe
                405                 410                 415
His Ser Met Tyr Ala His Ser Gln Ser Leu Asp Arg Leu Met Asn Pro
            420                 425                 430
Leu Leu Asp Gln Tyr Leu Trp Glu Leu Gln Ser Thr Thr Ser Gly Gly
        435                 440                 445
Thr Leu Asn Gln Gly Asn Ser Ala Thr Asn Phe Ala Lys Leu Thr Lys
    450                 455                 460
Thr Asn Phe Ser Gly Tyr Arg Lys Asn Trp Leu Pro Gly Pro Met Met
465                 470                 475                 480
Lys Gln Gln Arg Phe Ser Lys Thr Ala Ser Gln Asn Tyr Lys Ile Pro
                485                 490                 495
Gln Gly Arg Asn Asn Ser Leu Leu His Tyr Glu Thr Arg Thr Thr Leu
            500                 505                 510
Asp Gly Arg Trp Ser Asn Phe Ala Pro Gly Thr Ala Met Ala Thr Ala
        515                 520                 525
Ala Asn Asp Ala Thr Asp Phe Ser Gln Ala Gln Leu Ile Phe Ala Gly
    530                 535                 540
Pro Asn Ile Thr Gly Asn Thr Thr Thr Asp Ala Asn Asn Leu Met Phe
545                 550                 555                 560
Thr Ser Glu Asp Glu Leu Arg Ala Thr Asn Pro Arg Asp Thr Asp Leu
                565                 570                 575
Phe Gly His Leu Ala Thr Asn Gln Gln Asn Ala Thr Thr Val Pro Thr
            580                 585                 590
Val Asp Asp Val Asp Gly Val Gly Val Tyr Pro Gly Met Val Trp Gln
        595                 600                 605
Asp Arg Asp Ile Tyr Tyr Gln Gly Pro Ile Trp Ala Lys Ile Pro His
    610                 615                 620
Thr Asp Gly His Phe His Pro Ser Pro Leu Ile Gly Gly Phe Gly Leu
625                 630                 635                 640
Lys Ser Pro Pro Pro Gln Ile Phe Ile Lys Asn Thr Pro Val Pro Ala
                645                 650                 655
Asn Pro Ala Thr Thr Phe Ser Pro Ala Arg Ile Asn Ser Phe Ile Thr
            660                 665                 670
Gln Tyr Ser Thr Gly Gln Val Ala Val Lys Ile Glu Trp Glu Ile Gln
        675                 680                 685
Lys Glu Arg Ser Lys Arg Trp Asn Pro Glu Val Gln Phe Thr Ser Asn
    690                 695                 700
Tyr Gly Ala Gln Asp Ser Leu Leu Trp Ala Pro Asp Asn Ala Gly Ala
705                 710                 715                 720
```

```
Tyr Lys Glu Pro Arg Ala Ile Gly Ser Arg Tyr Leu Thr Asn His Leu
            725                 730                 735
```

<210> SEQ ID NO 7
<211> LENGTH: 44
<212> TYPE: DNA
<213> ORGANISM: Artificial
<220> FEATURE:
<223> OTHER INFORMATION: forward primer 1

<400> SEQUENCE: 7
gtgcccttct acggctgcgt caactggacc aatgagaact ttcc          44

<210> SEQ ID NO 8
<211> LENGTH: 32
<212> TYPE: DNA
<213> ORGANISM: Artificial
<220> FEATURE:
<223> OTHER INFORMATION: reverse primer 2

<400> SEQUENCE: 8
ggaatcgcaa tgccaatttc ctgaggcatt ac                       32

<210> SEQ ID NO 9
<211> LENGTH: 29
<212> TYPE: DNA
<213> ORGANISM: Artificial
<220> FEATURE:
<223> OTHER INFORMATION: forward primer

<400> SEQUENCE: 9
aaatcaggta tgtcttttgt tgatcaccc                           29

<210> SEQ ID NO 10
<211> LENGTH: 43
<212> TYPE: DNA
<213> ORGANISM: Artificial
<220> FEATURE:
<223> OTHER INFORMATION: reverse primer

<400> SEQUENCE: 10
acacgaatta accggtttat tgagggtatg cgacatgaat ggg           43

<210> SEQ ID NO 11
<211> LENGTH: 44
<212> TYPE: DNA
<213> ORGANISM: Artificial
<220> FEATURE:
<223> OTHER INFORMATION: forward primer

<400> SEQUENCE: 11
gtgcccttct acggctgcgt caactggacc aatgagaact ttcc          44

<210> SEQ ID NO 12
<211> LENGTH: 32
<212> TYPE: DNA
<213> ORGANISM: Artificial
<220> FEATURE:
<223> OTHER INFORMATION: reverse primer

<400> SEQUENCE: 12
ggaatcgcaa tgccaatttc ctgaggcatt ac                       32

<210> SEQ ID NO 13
<211> LENGTH: 29
<212> TYPE: DNA

```
<213> ORGANISM: Artificial
<220> FEATURE:
<223> OTHER INFORMATION: PCR primer

<400> SEQUENCE: 13
aaatcaggta tgtcttttgt tgatcaccc                                29

<210> SEQ ID NO 14
<211> LENGTH: 43
<212> TYPE: DNA
<213> ORGANISM: Artificial
<220> FEATURE:
<223> OTHER INFORMATION: PCR primer

<400> SEQUENCE: 14
acacgaatta accggtttat tgagggtatg cgacatgaat ggg                43
```

AAV VECTORS FOR GENE DELIVERY TO THE LUNG

CROSS-REFERENCE TO RELATED APPLICATIONS

This application is a divisional application of U.S. patent application Ser. No. 11/143,866, filed Jun. 2, 2005 from which priority is claimed pursuant to 35 U.S.C. §120, and claims benefit under 35 U.S.C. §119(e) of provisional applications 60/576,506 filed Jun. 3, 2004 and 60/582,037 filed Jun. 21, 2004, which applications are hereby incorporated by reference in their entireties.

TECHNICAL FIELD

The present invention relates generally to compositions and methods for delivering genes to cells using recombinant adeno-associated virus (rAAV) virions. In particular, the present invention pertains to rAAV virions with tropism for lung tissue.

BACKGROUND

A number of lung disorders are genetically based. For example, cystic fibrosis (CF) is one of the most common, life-threatening, autosomal recessive diseases. Approximately 1 in 2,500 live births is affected by this genetic disorder. Patients with CF usually die at an early age due to lung infection. The disease is caused by a mutation of the cystic fibrosis transmembrane conductance regulator (CFTR) gene.

Similarly, alpha-1-antitrypsin deficiency is the second most common monogenic lung disease in humans, accounting for approximately 3% of all early deaths due to obstructive pulmonary disease such as pulmonary emphysema. The most common type of alpha-1-antitrypsin deficiency, termed protease inhibitor type Z (PiZ), is transmitted as an autosomal recessive trait and affects approximately 1 in 1700 live births in most Northern European and North American populations. The PiZ mutation is a single nucleotide substitution that results in a single amino acid substitution (glutamate 342 to lysine). The replacement of glutamate 342 with a lysine apparently prevents normal folding of the protein.

At present, treatment options for individuals with CF, as well as for patients with pathologies associated with alpha-1-antitrypsin deficiency, are limited. Accordingly, it would be desirable to develop gene therapy techniques to deliver genes to the lungs of subjects suffering from these and other lung disorders.

Gene transfer techniques have been developed in order to introduce DNA into a patient's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery vectors include those based on retrovirus, adenovirus, herpes virus, pox virus, and adeno-associated virus (AAV). Like the retroviruses, and unlike adenovirus, AAV has the ability to integrate its genome into a host cell chromosome.

AAV is a parvovirus belonging to the genus *Dependovirus*, and has several attractive features not found in other viruses. For example, AAV can infect a wide range of host cells, including non-dividing cells. AAV can also infect cells from different species. Importantly, AAV has not been associated with any human or animal disease, and does not appear to alter the physiological properties of the host cell upon integration. Furthermore, AAV is stable at a wide range of physical and chemical conditions, which lends itself to production, storage, and transportation requirements.

The AAV genome, a linear, single-stranded DNA molecule containing approximately 4700 nucleotides (the AAV-2 genome consists of 4681 nucleotides), generally comprises an internal non-repeating segment flanked on each end by inverted terminal repeats (ITRs). The ITRs are approximately 145 nucleotides in length (AAV-1 has ITRs of 143 nucleotides) and have multiple functions, including serving as origins of replication, and as packaging signals for the viral genome.

The internal non-repeated portion of the genome includes two large open reading frames (ORFs), known as the AAV replication (rep) and capsid (cap) regions. These ORFs encode replication and capsid gene products, respectively: replication and capsid gene products (i.e., proteins) allow for the replication, assembly, and packaging of a complete AAV virion. More specifically, a family of at least four viral proteins are expressed from the AAV rep region: Rep 78, Rep 68, Rep 52, and Rep 40, all of which are named for their apparent molecular weights. The AAV cap region encodes at least three proteins: VP1, VP2, and VP3.

In nature, AAV is a helper virus-dependent virus, i.e., it requires co-infection with a helper virus (e.g., adenovirus, herpesvirus, or vaccinia virus) in order to form functionally complete AAV virions. In the absence of co-infection with a helper virus, AAV establishes a latent state in which the viral genome inserts into a host cell chromosome or exists in an episomal form, but infectious virions are not produced. Subsequent infection by a helper virus "rescues" the integrated genome, allowing it to be replicated and packaged into viral capsids, thereby reconstituting the infectious virion. While AAV can infect cells from different species, the helper virus must be of the same species as the host cell. Thus, for example, human AAV will replicate in canine cells that have been co-infected with a canine adenovirus.

To construct infectious recombinant AAV (rAAV) containing a nucleic acid, a suitable host cell line is transfected with an AAV vector containing a nucleic acid. AAV helper functions and accessory functions are then expressed in the host cell. Once these factors come together, the HNA is replicated and packaged as though it were a wild-type (wt) AAV genome, forming a recombinant virion. When a patient's cells are infected with the resulting rAAV, the HNA enters and is expressed in the patient's cells. Because the patient's cells lack the rep and cap genes, as well as the adenovirus accessory function genes, the rAAV are replication defective; that is, they cannot further replicate and package their genomes. Similarly, without a source of rep and cap genes, wtAAV cannot be formed in the patient's cells.

There are several AAV serotypes that infect humans as well as other primates and mammals. Eight major serotypes have been identified, AAV-1 through AAV-8, including two serotypes recently isolated from rhesus monkeys. Gao et al. (2002) *Proc. Natl. Acad. Sci. USA* 99:11854-11859. Of those serotypes, AAV-2 is the best characterized, having been used to successfully deliver transgenes to several cell lines, tissue types, and organs in a variety of in vitro and in vivo assays. The various serotypes of AAV can be distinguished from one another using monoclonal antibodies or by employing nucleotide sequence analysis; e.g., AAV-1, AAV-2, AAV-3, and AAV-6 are 82% identical at the nucleotide level, while AAV-4 is 75 to 78% identical to the other serotypes (Russell et al. (1998) *J. Virol.* 72:309-319). Significant nucleotide sequence variation is noted for regions of the AAV genome that code for capsid proteins. Such variable regions may be responsible for differences in serological reactivity to the capsid proteins of the various AAV serotypes.

It would be desirable to develop AAV-based vectors with tropism to lung tissue in order to effectively treat lung disorders.

SUMMARY OF THE INVENTION

The present invention is based on the discovery of novel AAV variants with tropism to lung tissue. The AAV variants are derived from a caprine source and from a bovine source. The rAAV virions made using caprine and bovine AAV sequences are able to efficiently transduce lung cells and tissues and are especially useful for delivering heterologous nucleic acid molecules (HNAs) to subjects with lung disorders. Moreover, the caprine and bovine AAV sequences display significantly decreased immunoreactivity relative to rAAV virions typically used in gene therapy studies. Thus, subjects that have been previously exposed to AAV, either by natural infection or due to previous gene therapy or nucleic acid immunization treatments, and have therefore developed anti-AAV antibodies, can still benefit from the use of the caprine and bovine rAAV virions of the invention. Moreover, the caprine and bovine rAAV virions described herein are readily administered and display efficient transduction using a vascular route of administration. Thus delivery can be achieved by simple intravenous administration rather than via the airway, which is often highly damaged in serious lung disorders.

The rAAV virions described herein are therefore useful for treating or preventing a wide variety of lung disorders in vertebrate subjects in need of such treatment, whether or not the subject has been previously exposed to any of the various AAV serotypes.

In one aspect, the present invention provides methods and AAV vectors for the efficient delivery of HNAs, such as a gene of interest, to the lung cells or tissue of a vertebrate subject, such as a human, to provide a therapeutic effect. In certain preferred embodiments, rAAV virions are derived from caprine AAV In other rAAV virions are derived from bovine AAV. In some embodiments the rAAV virions comprise an HNA encoding antisense RNA, ribozymes, or one or more genes of interest that express proteins. The rAAV virions can be used to deliver these HNAs to the lung, wherein expression of said antisense RNA, ribozymes, or genes in lung cells or tissue provides for a biological effect in a mammalian subject.

Thus, in one aspect, the invention is directed to a method for delivering HNAs to the lung of a vertebrate subject using an rAAV virion. In one embodiment, the method comprises (a) providing a caprine rAAV virion, wherein the virion comprises a heterologous nucleic acid molecule encoding a therapeutic protein operably linked to control elements capable of directing the in vivo transcription and translation of said protein; and (b) delivering the recombinant AAV virion to the vertebrate subject, whereby the protein is expressed in the lung at a level that provides a therapeutic effect. In another embodiment, a bovine rAAV virion is used instead of the caprine rAAV in the method of the previous sentence.

In another embodiment, the rAAV virions containing an HNA are injected directly into a muscle (e.g., cardiac, smooth and/or skeletal muscle). In another embodiment the rAAV virions containing an HNA are administered into the vasculature via injection into veins, arteries, or other vascular conduits, or by using techniques such as isolated limb perfusion.

In an additional embodiment, the virions contain a gene encoding CFTR, the gene deficient or missing in cystic fibrosis patients, that when expressed at a sufficient concentration provides for a therapeutic effect, such as amelioration or reduction of symptoms caused by cystic fibrosis.

In another embodiment the virions contain a gene encoding alpha-1-antitrypsin that when expressed at a sufficient concentration provides for a therapeutic effect, such as amelioration or reduction of symptoms caused by alpha-1-antitrypsin deficiency (e.g. emphysema).

In another embodiment, the virions contain a gene encoding an enzyme capable of removing toxic metabolites that tend to accumulate in diseased lung tissue (e.g. such as superoxide dismutase (SOD) and catalase) that when expressed at a sufficient concentration, provides for a therapeutic effect, such as amelioration or reduction of the toxic metabolites.

In yet a further embodiment, the virions contain a gene encoding an anti-tumor agent or a tumor suppressor that when expressed at a sufficient concentration provides for a therapeutic effect, such as a reduction in tumor size and/or growth. Such agents include immunomodulators, such as any of the various cytokines including interleukin-1, interleukin-2, interleukin-3, interleukin-4, and gamma-interferon; p53; the retinoblastoma (rb) gene product; antisense oncogenes, e.g., anti-c-myc and anti-k-ras; and other growth control-related genes for cancer gene therapy.

In additional embodiments, the virions contain a gene encoding an agent useful for treating primary pulmonary hypertension, pulmonary vascular disease secondarily associated with chronic airways obstruction, and connective tissue diseases.

In further embodiments, the invention is directed to a recombinant AAV virion comprising any of the HNAs described above.

In yet further embodiments, the invention is directed to a method of delivering an HNA to a lung cell or tissue of a vertebrate subject using a recombinant caprine or bovine AAV virion. The method comprises:

(a) providing a recombinant caprine or bovine AAV virion as above, wherein the virion comprises an HNA encoding a protein;

(b) administering the recombinant AAV virion to the subject, whereby the protein is expressed at a level in lung cells or tissue that provides a therapeutic effect.

In certain embodiments, the recombinant AAV virion is delivered by intramuscular injection, or into the bloodstream (e.g. intravenously or intraarterially).

These and other embodiments of the subject invention will readily occur to those of skill in the art in view of the disclosure herein.

BRIEF DESCRIPTION OF THE FIGURES

FIGS. 2A-2B show a comparison of the nucleotide sequence encoding the AAV VP1 protein from a primate AAV-5 (SEQ ID NO:1) and a caprine AAV (SEQ ID NO:3). Numbering is relative to the AAV-5 full-length sequence.

FIG. 3 shows a comparison of the amino acid sequence of VP 1 from a primate AAV-5 (SEQ ID NO:2) and a caprine AAV (SEQ ID NO:4). Amino acid differences are shaded. Conservative changes are shown in light grey; non-conservative changes are shown in dark grey.

FIG. 5 shows a comparison of the amino acid sequence of the capsid proteins (VP1) of bovine AAV disclosed herein (SEQ ID NO:5) and a previously reported bovine AAV (Schmidt at al. (2004) *J. Virol.* 78:6509-16) (SEQ ID NO:6), referred to herein as "Schmidt bovine AAV." Amino acid differences are shown, and the dots in the alignment represent identical amino acids. Accessibility and Surface Feature designations are provided based on the AAV-2 crystal structure, in which B refers to amino acids buried between inside and outside surface; 0 refers to amino acids on outside surface; P refers to amino acids in a plateau; and S refers to amino acids in a spike FIGS. 6A and 6B show the transduction of muscle in SCID mice by bovine AAV, AAV-8 and AAV-1. Male mice were injected intramuscularly with $2 \times 10^{11}$ vector genomes of bovine rAAV hFIX9 (◆) in FIG. 6A, and AAV-1 (▲) and AAV-8 (■) in FIG. 6B. Human factor IX concentration was measured by ELISA. Each data point corresponds to the mean of five animals. The human factor IX concentration in the control animals was considered as a blank, and was subtracted from human factor IX levels in the experimental animals.

DETAILED DESCRIPTION OF THE INVENTION

Figure 1:
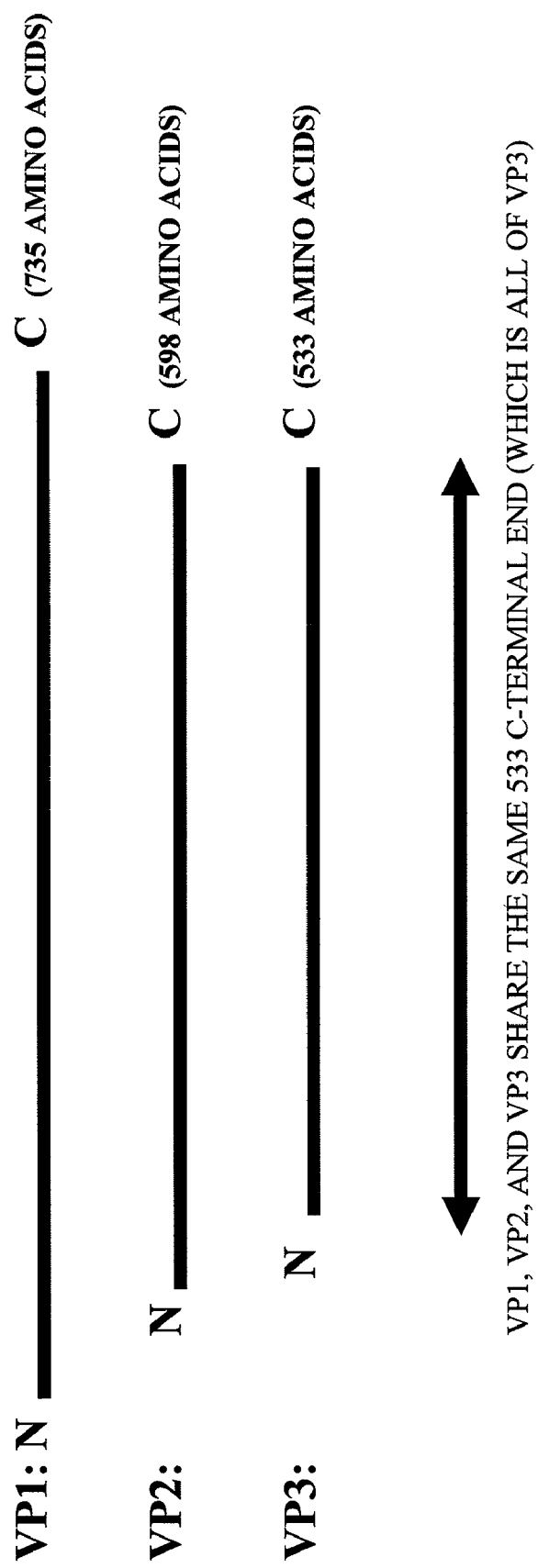
FIG. 1 shows the positions of capsid proteins VP1, VP2 and VP3, numbered relative to AAV-2. As shown in the figure, VP1, VP2 and VP3 share the same 533 C-terminal amino acids, which make up VP3.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein are hereby incorporated by reference in their entireties.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from any adeno-associated virus serotype isolated from any animal species, including without limitation, AAV-1, AAV-2, AAV-3, AAV-4, AAV-5, AAV-6, AAV-7, AAV-8 and caprine AAV (AAV-G1) as described herein. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs and vectors that encode Rep and/or Cap expression products have been described. See, e.g., U.S. Pat. Nos. 6,001,650, 5,139,941 and 6,376,237, all incorporated herein by reference in their entireties; Samulski et al. (1989) *J. Virol.* 63:3822-3828; and McCarty et al. (1991) *J. Virol.* 65:2936-2945. Particularly useful herein are AAV helper constructs including a caprine cap gene, such as a caprine VP1 protein, or a bovine cap gene, such as a bovine VP1 protein.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

It has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions*, in I *CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, recently reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus including an AAV protein shell, encapsidating a heterologous nucleotide sequence of interest that is flanked on both sides by AAV ITRs. A rAAV virion is produced in a suitable host cell that has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

A "caprine recombinant AAV virion" or "caprine rAAV virion" is a rAAV virion as described above that has been produced using AAV helper functions that include a gene encoding a caprine capsid protein, such as caprine VP1.

A "bovine recombinant AAV virion" or "bovine rAAV virion" is a rAAV virion as described above that has been produced using AAV helper functions that include a gene encoding a bovine capsid protein, such as bovine VP1.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) Gene 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct that is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N-6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "5 prime (5')" or "3 prime (3')" relative to another sequence, it is to be understood that it is the position of the sequences in the "sense" or "coding" strand of a DNA molecule that is being referred to as is conventional in the art.

A "functional homologue," or a "functional equivalent" of a given AAV polypeptide includes molecules derived from the native polypeptide sequence, as well as recombinantly produced or chemically synthesized polypeptides which function in a manner similar to the reference AAV molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

By "capable of efficient transduction" is meant that the mutated constructs of the invention provide for rAAV vectors or virions that retain the ability to transfect cells in vitro and/or in vivo at a level that is within 1-10% of the transfection efficiency obtained using the corresponding wild-type sequence. Preferably, the mutant retains the ability to transfect cells or tissues at a level that is within 10-100% of the corresponding wild-type sequence. The mutated sequence may even provide for a construct with enhanced ability to transfect cells and tissues. Transduction efficiency is readily determined using techniques well known in the art, including the in vitro transduction assay described in the Examples.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "effective amount" or "therapeutically effective amount" of a composition or agent, as provided herein, refer to a nontoxic but sufficient amount of the composition or agent to provide the desired response. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treating" or "treatment" of a disease includes: (1) preventing the disease, i.e. causing the clinical symptoms of the disease not to develop in a subject that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

2. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery of novel caprine and bovine AAV sequences useful in the production of rAAV virions that display remarkable lung tropism. Thus, AAV vectors and virions derived from these caprine and bovine AAV sequences are useful for targeting gene delivery to lung cells and tissue. Delivery of genes to the pulmonary vascular endothelium is a rational approach for therapy of pulmonary vascular diseases including, but not limited to, primary pulmonary hypertension, pulmonary vascular disease secondarily associated with chronic airways obstruction, connective tissue diseases, HIV infection, and emphysema. Furthermore, in view of the exposure of this vascular bed to the entire cardiac output, delivery to the lungs is useful to achieve systhemic delivery of secreted factors. Aside from vascular disease per se, the pulmonary bed is frequently the site of metastatic spread of malignancy, and once this occurs conventional therapy options are most often inadequate.

Thus, the vectors and virions find use in the treatment of a wide variety of lung disorders, including without limitation, cystic fibrosis (CF), alpha-1-antitrypsin gene deficiencies, lung cancer, lung deterioration caused by degenerative lung diseases, and pulmonary vascular disease.

For example, it is known that CF is caused by a mutation of the cystic fibrosis transmembrane conductance regulator (CFTR) gene. Thus rAAV virions containing a gene encoding CFTR can be administered to patients suffering from CF to provide for a therapeutic effect, such as amelioration or reduction of symptoms caused by cystic fibrosis.

Similarly, a common type of alpha-1-antitrypsin deficiency, termed protease inhibitor type Z (PiZ), is caused by a single nucleotide substitution that results in a single amino acid substitution (glutamate 342 to lysine). The replacement of glutamate 342 with a lysine apparently prevents normal folding of the protein. Thus, rAAV virions containing a gene encoding the wild-type alpha-1-antitrypsin can be administered to patients suffering from alpha-1-antitrypsin to provide for a therapeutic effect, such as amelioration or reduction of symptoms caused by alpha-1-antitrypsin deficiency, such as emphysema.

Additionally, the rAAV vectors and virions of the present invention can also be used to deliver genes to patients with degenerative diseases of the lung, e.g., genes encoding enzymes capable of removing toxic metabolites which tend to accumulate in diseased lung tissue, such as superoxide dismutase (SOD) and catalase.

The caprine and bovine AAV vectors and virions of the present invention are also useful for treating cancers of the lung. For example, the caprine and bovine AAV vectors and virions can be used to deliver a gene encoding an anti-tumor agent or a tumor suppressor, that when expressed at a sufficient concentration, provides for a therapeutic effect, such as a reduction in tumor size and/or growth. Such agents include immunomodulators, such as any of the various cytokines including interleukin-1, interleukin-2, interleukin-3, interleukin-4, and gamma-interferon; p53; the retinoblastoma (rb) gene; antisense oncogenes, e.g., anti-c-myc and anti-k-ras; and other growth control-related genes for cancer gene therapy.

Moreover, because the pulmonary vasculature bed is exposed to the entire cardiac output, delivery of a gene of interest to the lungs is useful to achieve systhemic delivery of a large number of secreted factors, including but not limited to, one or more peptides, polypeptides, or proteins that are useful for the treatment or prevention of disease states in a mammalian subject. Such DNA and associated disease states include, but are not limited to: DNA encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain alpha-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding ornithine transcarbamylase, associated with ornithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotimidase, associated with biotimidase deficiency; DNA encoding beta-glucocerebrosidase, associated with Gaucher disease; DNA encoding beta-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding erythropoietin for treatment of anemia due to thalassemia or to renal failure; DNA encoding vascular endothelial growth factor, DNA encoding angiopoietin-1, and DNA encoding fibroblast growth factor for the treatment of ischemic diseases; DNA encoding thrombomodulin and tissue factor pathway inhibitor for the treatment of occluded blood vessels as seen in, for example, atherosclerosis, thrombosis, or embolisms; DNA encoding aromatic amino acid decarboxylase (AADC), and DNA encoding tyrosine hydroxylase (TH) for the treatment of Parkinson's disease; DNA encoding the beta adrenergic receptor, DNA encoding anti-sense to, or DNA encoding a mutant form of, phospholamban, DNA encoding the sarco(endo)plasmic reticulum adenosine triphosphatase-2 (SERCA2), and DNA encoding the cardiac adenylyl cyclase for the treatment of congestive heart failure; DNA encoding a tumor suppressor gene such as p53 for the treatment of various cancers, including lung cancer; DNA encoding a cytokine such as one of the various interleukins for the treatment of inflammatory and immune disorders and cancers; DNA encoding dystrophin or minidystrophin and DNA encoding utrophin or miniutrophin for the treatment of muscular dystrophies; and, DNA encoding insulin for the treatment of diabetes.

The invention also provides caprine and bovine rAAV virions comprising a gene or genes coding for blood coagulation proteins, which proteins may be delivered, using the methods of the present invention, to the lung of a mammal having hemophilia for the treatment of hemophilia. Thus, the invention includes: delivery of the Factor IX gene to a mammal for treatment of hemophilia B, delivery of the Factor VIII gene to a mammal for treatment of hemophilia A, delivery of the Factor VII gene for treatment of Factor VII deficiency, delivery of the Factor X gene for treatment of Factor X deficiency, delivery of the Factor XI gene for treatment of Factor XI deficiency, delivery of the Factor XIII gene for treatment of Factor XIII deficiency, and, delivery of the Protein C gene for treatment of Protein C deficiency. Delivery of each of the above-recited genes to the cells of a mammal is accomplished by first generating a caprine and bovine rAAV virion comprising the gene and then administering the rAAV virion to the mammal. Thus, the invention includes rAAV virions comprising genes encoding any one of Factor IX, Factor VIII, Factor X, Factor VII, Factor XI, Factor XIII or Protein C.

Generally, caprine rAAV virions will include at least a caprine AAV capsid protein, and the bovine rAAV virions will include at least a bovine AAV capsid protein. Thus, by "caprine rAAV virion" is meant an rAAV virion that includes at least one caprine capsid protein, and by "bovine rAAV virion" is meant an rAAV virion that includes at least one bovine capsid protein. As explained above, the AAV cap region encodes at least three proteins: VP1, VP2, and VP3. FIG. 1 shows the overlapping structure of this region from AAV-2 which is similar to the caprine structure (see further below). Preferably, the rAAV virions include at least the caprine VP3 region, but can include the entire VP2 or VP1 region. The caprine AAV VP1 sequence is highly homologous to the VP1 sequence of AAV-5, but is approximately 100 times more resistant to neutralization by existing AAV antibodies than the native AAV-5 sequence.

More particularly, a 2805 b PCR fragment of the caprine AAV described herein, encoding 603 bp of rep, the central intron, and all of cap, shows 94% homology to the corresponding AAV-5 sequence. The DNA and protein homologies for the partial rep are 98% and 99%, respectively. A comparison of the caprine VP1 coding sequence with a primate AAV-5 VP1 coding sequence is shown in FIGS. 2A-2B. The DNA for the cap region of the caprine AAV is 93% homologous to that of AAV-5. The amino acid sequences for the caprine VP1 versus a primate AAV-5 is shown in FIG. 3. The caprine sequence encodes a VP1 protein of 726 amino acids, while AAV-5 VP1 is 724 amino acids in length. Additionally, the sequences display 94% sequence identity and 96% sequence similarity. There are 43 amino acid differences between the caprine and the primate AAV-5 VP1 sequence. With respect to the linear amino acid sequence of VP1, the distribution of the amino acid differences between AAV-5 and caprine AAV is highly polar. All of the amino acid differences occur exclusively in the C-terminal hypervariable region of VP1 in a scattered fashion. This region relative to AAV-5 and caprine includes approximately 348 amino acids from amino acid 386 to the C-terminus, numbered relative to AAV-5 VP1.

Moreover, rAAV virions including such caprine sequences show substantial tropism to lung tissue. Thus, the present invention involves the production and use of caprine AAV sequences for incorporation into rAAV virions. Such rAAV virions can be used to deliver a "heterologous nucleic acid" (an "HNA") to the lung tissue of a vertebrate subject, such as a mammal. As explained above, a "recombinant AAV virion" or "rAAV virion" is an infectious virus composed of an AAV protein shell (i.e., a capsid), derived from caprine AAV, encapsulating a "recombinant AAV (rAAV) vector," the rAAV vector comprising the HNA and one or more AAV inverted terminal repeats (ITRs). AAV vectors can be constructed using recombinant techniques that are known in the art and include one or more HNAs flanked by functional ITRs. The ITRs of the rAAV vector need not be the wild-type nucleotide sequences, and may be altered, e.g., by the insertion, deletion, or substitution of nucleotides, so long as the sequences provide for proper function, i.e., rescue, replication, and packaging of the AAV genome.

Recombinant AAV virions may be produced using a variety of techniques known in the art, including the triple transfection method (described in detail in U.S. Pat. No. 6,001,650, the entirety of which is incorporated herein by reference). This system involves the use of three vectors for rAAV virion production, including an AAV helper function vector, an accessory function vector, and a rAAV vector that contains the HNA. One of skill in the art will appreciate, however, that the nucleic acid sequences encoded by these vectors can be provided on two or more vectors in various combinations. As used herein, the term "vector" includes any genetic element, such as a plasmid, phage, transposon, cosmid, chromosome, artificial chromosome, virus, virion, etc., that is capable of replication when associated with the proper control elements and that can transfer gene sequences between cells. Thus, the term includes cloning and expression vehicles, as well as viral vectors.

The AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Examples of vectors suitable for use with the present invention include pHLP19, described in U.S. Pat. No. 6,001,650 and pRep6cap6 vector, described in U.S. Pat. No. 6,156,303, the disclosure of which is hereby incorporated by reference in its entirety.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. In a preferred embodiment, the accessory function plasmid pladeno5 is used (details regarding pLadeno5 are described in U.S. Pat. No. 6,004,797, the disclosure of which is hereby incorporated by reference in its entirety). This plasmid provides a complete set of adenovirus accessory functions for AAV vector production, but lacks the components necessary to form replication-competent adenovirus.

The rAAV vector containing the heterologous nucleic acid (HNA) may be constructed using ITRs from any of the various AAV serotypes. The RNA comprises nucleic acid sequences joined together that are otherwise not found together in nature, this concept defining the term "heterologous." To illustrate the point, an example of an HNA is a gene flanked by nucleotide sequences not found in association with that gene in nature. Another example of an HNA is a gene that itself is not found in nature (e.g., synthetic sequences having codons different from the native gene). Allelic variation or naturally occurring mutational events do not give rise to HNAs, as used herein. An HNA can comprise an anti-sense RNA molecule, a ribozyme, or a gene encoding a polypeptide.

The HNA is operably linked to a heterologous promoter (constitutive, cell-specific, or inducible) such that the HNA is capable of being expressed in the patient's target cells (here lung) under appropriate or desirable conditions. Numerous examples of constitutive, cell-specific, and inducible promoters are known in the art, and one of skill could readily select a promoter for a specific intended use, e.g., the selection of the constitutive CMV promoter for strong levels of continuous or near-continuous expression, or the selection of the inducible ecdysone promoter for induced expression. Induced expression allows the skilled artisan to control the amount of protein that is synthesized. In this manner, it is possible to vary the concentration of therapeutic product. Other examples of well known inducible promoters are: steroid promoters (e.g., estrogen and androgen promoters) and metallothionein promoters.

As explained above, in one embodiment, the invention relates to novel AAV virions including caprine and bovine capsids and comprising HNAs coding for one or more antisense RNA molecules, the rAAV virions preferably administered to one or more muscle cells or tissue of a mammal. Antisense RNA molecules suitable for use with the present invention in cancer anti-sense therapy or treatment of viral diseases have been described in the art. See, e.g., Han et al., (1991) *Proc. Natl. Acad. Sci. USA* 88:4313-4317; Uhlmann et al., (1990) *Chem. Rev.* 90:543-584; Helene et al., (1990) *Biochim. Biophys. Acta.* 1049:99-125; Agarawal et al., (1988) *Proc. Natl. Acad. Sci. USA* 85:7079-7083; and Heikkila et al., (1987) *Nature* 328:445-449. The invention also encompasses the delivery of ribozymes using the methods disclosed herein. For a discussion of suitable ribozymes, see, e.g., Cech et al., (1992) *J. Biol. Chem.* 267:17479-17482 and U.S. Pat. No. 5,225,347.

Preferably, the rAAV virions comprise HNAs coding for one or more polypeptides for treating a lung disorder. The rAAV virions are preferably administered to one or more cells or tissue of a mammal, and display tropism for lung. Thus, the invention embraces the delivery of HNAs encoding one or more peptides, polypeptides, or proteins, that are useful for the treatment or prevention of lung disease states in a mammalian subject. Such DNA and associated disease states are described above.

Delivery of the recombinant virions containing one or more HNAs to a mammalian subject may be by intramuscular injection or by administration into the bloodstream of the mammalian subject. Administration into the bloodstream may be by injection into a vein, an artery, or any other vascular conduit. The recombinant caprine and bovine virions of the invention may also be introduced into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403 and herein incorporated by reference, can also be employed by the skilled artisan to administer the virions into the vasculature of an isolated limb to potentially enhance transduction into lung cells or tissue.

The dose of rAAV virions required to achieve a particular "therapeutic effect," e.g., the units of dose in vector genomes/per kilogram of body weight (vg/kg), will vary based on several factors including, but not limited to: the route of rAAV virion administration, the level of gene (or anti-sense RNA or ribozyme) expression required to achieve a therapeutic effect, the specific disease or disorder being treated, a host immune response to the rAAV virion, a host immune response to the gene (or anti-sense RNA or ribozyme) expression product, and the stability of the gene (or anti-sense RNA or ribozyme) product. One of skill in the art can readily determine a rAAV virion dose range to treat a patient having a particular disease or disorder based on the aforementioned factors, as well as other factors that are well known in the art.

Generally speaking, by "therapeutic effect" is meant a level of expression of one or more HNAs sufficient to alter a component of a lung disease (or disorder) toward a desired outcome or clinical endpoint, such that a patient's disease or disorder shows clinical improvement, often reflected by the amelioration of a clinical sign or symptom relating to the disease or disorder.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Isolation and Characterization of a Caprine AAV

A. Cell Culture and Virus Isolation

Ovine adenovirus preparations with evidence of parvovirus contamination were isolated from caprine ileum as follows. Tissue was homogenized in Eagle's MEM medium containing Earles salts (pH 7.2) and gentamicin. The homogenate was clarified by low speed centrifugation (1,500×g) for 20 minutes and filter-sterilized though a 0.45 μm device. Supernatant (500 μl) was inoculated onto a 25 $cm^2$ flask containing primary cultures of fetal lamb kidney cells at passage 3 and incubated with fetal bovine serum (USA) and lactalbumin hydrolysate (USA) at 37° C. in humid, 5% $CO_2$ incubator for one week. Cells were trypsinized, split, and incubated again as described above and finally assayed for typical adenoviral cytophatic effect (CPE). Flasks showing CPE were frozen at −70° C., thawed and layered onto other cell types. These flasks were later incubated and tested for CPE.

Other cell types used included non-immortalized (passage 8) ovine fetal turbinate cells derived from fetal ovine tissue and Maden Darby bovine kidney cells, maintained by long-term passage (used at passage 160). Porcine trypsin (USA) was used in all tissue culture processes and no human cell cultures or products were used.

B. Viral DNA Isolation and AAV Sequence Identification and Comparison

Four preparations from different cell cultures and passages were processed individually for DNA extraction. Virus-containing supernatant was treated with proteinase K (200 μg) in digestion buffer (10 mM Tris-HCl (pH 8.0), 10 mM EDTA (pH 8.0) and 0.5% SDS) and incubated at 37° C. for 1 hour. Following phenol chloroform extraction and ethanol precipitation the viral DNA was resuspended in TE. The DNA content of each preparation was determined by PicoGreen DNA quantitation (Molecular Probes, Eugene, Oreg.) and the preparations were diluted to 20 ng/μl to standardize DNA concentration for subsequent PCR assays.

Oligonucleotide Primers

Oligonucleotide primers were selected on the basis of sequence alignments from segments that were highly conserved among known AAVs. The forward primer 1 (GTGCCCTTCTACGGCTGCGTCAACTGGAC-CAATGAGAACTTTCC) (SEQ ID NO:7), was complementary to the helicase domain and the reverse primer 2 (GGAATCGCAATGCCAATTTCCTGAGGCATTAC) (SEQ ID NO:8), was complementary to the DNA binding domain. The expected size of PCR fragments was 1.5 kb.

PCR Amplifications

All reactions were performed in 50 μl in an automated Eppendorf Mastercycler® Gradient thermocycler (Perkin Elmer, Boston, Mass.). Each reaction mixture contained 200 ng of template DNA, 1 μM each oligonucleotide primer, 1 mM $Mn(OAc)_2$, 200 μM each deoxynucleoside triphosphate (dATP, dCTP, dGTP, and dTTP), and 1.0 unit of rTth polymerase, XL (Applied Biosystems, Foster City, Calif.) in 1×XL Buffer II. Ampliwax® PCR gem 100 was used to facilitate hot start (Applied Biosystems, Foster City, Calif.).

Cycling conditions were as follows: 2 min of denaturation at 94° C., followed by 35 cycles of 15 s of denaturation at 94° C., 30 s of annealing at 45° C., and 2 min of elongation at 72° C.

PCR products (10 μl) were electrophoretically separated in a 1% NuSieve® agarose gel (FMC BioProducts, Rockland, Minn.), stained with ethidium bromide, and visualized by UV light. DNA molecular markers were used on each gel to facilitate the determination of the sizes of the reaction products.

To control for specificity of the assay, PCR was also performed with 100 ng of DNA from a plasmid containing AAV2 sequences.

DNA Sequencing

PCR products were purified on 1% low-melting agarose gels (FMC Bioproducts, Rockland, Me.), and the sequences were determined using primers designed from AAV-5 sequences. Sequence data were analyzed with the NTI vector suite software package (InforMax, Frederick, Md.).

Virus preparations from different cell cultures and passages were processed individually for DNA extraction and PCR analysis. PCR amplification using primers forward 1 and reverse 2 revealed the presence of parvovirus-like sequences in all four preparations. Sequence analysis revealed the presence of AAV sequences. The VP1 ORF of caprine AAV, corresponding to nucleotides 2,207 to 4,381 of AAV-5 genome, has 93% nucleotide identity (2,104/2,266, Gaps 6/2,266) with primate AAV-5 (see FIGS. 2A-2B) isolated from humans (*J. Virol* 1999; 73:1309-1319). Protein comparison showed 94% identity (682/726) and 96% similarity (698/726) between the primate AAV-5 and caprine AAV VP1 proteins (see, FIG. 3). Most if not all mutations appeared to be on the surface.

EXAMPLE 2

Lung Tropism of Caprine AAV

In order to determine the biodistribution of vector genomes derived from caprine AAV following administration, the following experiment was conducted. Male SCID mice (15-25 g) were injected via the tail vein with $5 \times 10^{11}$ vector genomes of caprine rAAV hF.IX (also referred to as rAAV-G1 hF.IX). In particular, the virions were generated using plasmid pAAV-hFIX16, containing the human factor IX gene under the control of a liver-specific promoter (described in Miao et al., *Mol. Ther.* (2000) 1:522-532). Plasmid pAAV-hFIX16 is an 11,277 bp plasmid encoding a human Factor IX minigene. In this construct, the FIX cDNA is interrupted between exons 1 and 2 with a deleted form of intron 1 that has been shown to increase expression of FIX. FIX expression is under the transcriptional control of the ApoE hepatic control region (HCR) and the human alpha 1 antitrypsin promoter (hAAT), as well as a bovine growth hormone polyadenylation signal (gGH PA). The backbone of plasmid pAAV-hFIX16 contains the β-lactamase gene, conferring ampicillin resistance, a bacterial origin of replication, a M13/F1 origin of replication, and a fragment of bacteriophage lambda DNA. The lambda DNA increases the size of the plasmid backbone to 6,966 bp, which prevents its packaging during AAV vector production.

The recombinant AAV virions were produced using the triple transfection method (described in detail in U.S. Pat. No. 6,001,650, incorporated herein by reference in its entirety), with the exception that the VP1 coding sequence present in plasmid pHLP19 (described in U.S. Pat. No. 6,001,650, incorporated herein by reference in its entirety) was substituted with the caprine VP1 coding sequence. Briefly, plasmid pHLP19 was digested with SwaI and AgeI (New England Biolabs, Beverly, Mass. 01915-5599), the fragment of interest was purified on a 1% low-melting agarose gel (FMC Bioproducts, Rockland, Me.), and used for ligation with the PCR fragment containing the caprine capsid. The caprine capsid PCR fragment was amplified using a forward primer: AAATCAGGTATGTCTTTTGTTGATCACCC (SEQ ID NO:9) and a reverse primer: ACACGAATTAACCGGTT-TATTGAGGGTATGCGACATGAATGGG (SEQ ID NO: 10). The PCR fragment was digested with the enzyme AgeI (New England Biolabs, Beverly, Mass. 01915-5599) and used for ligation with the digested plasmid.

For biodistribution analysis, mice were sacrificed and organs were collected 4 weeks after vector injection. Organs collected included-brain, testis, muscle (quadriceps), kidney, spleen, lung, heart, and liver. To measure HF.IX, quantitative-PCR was done on DNA samples extracted from different tissues.

Figure 4:
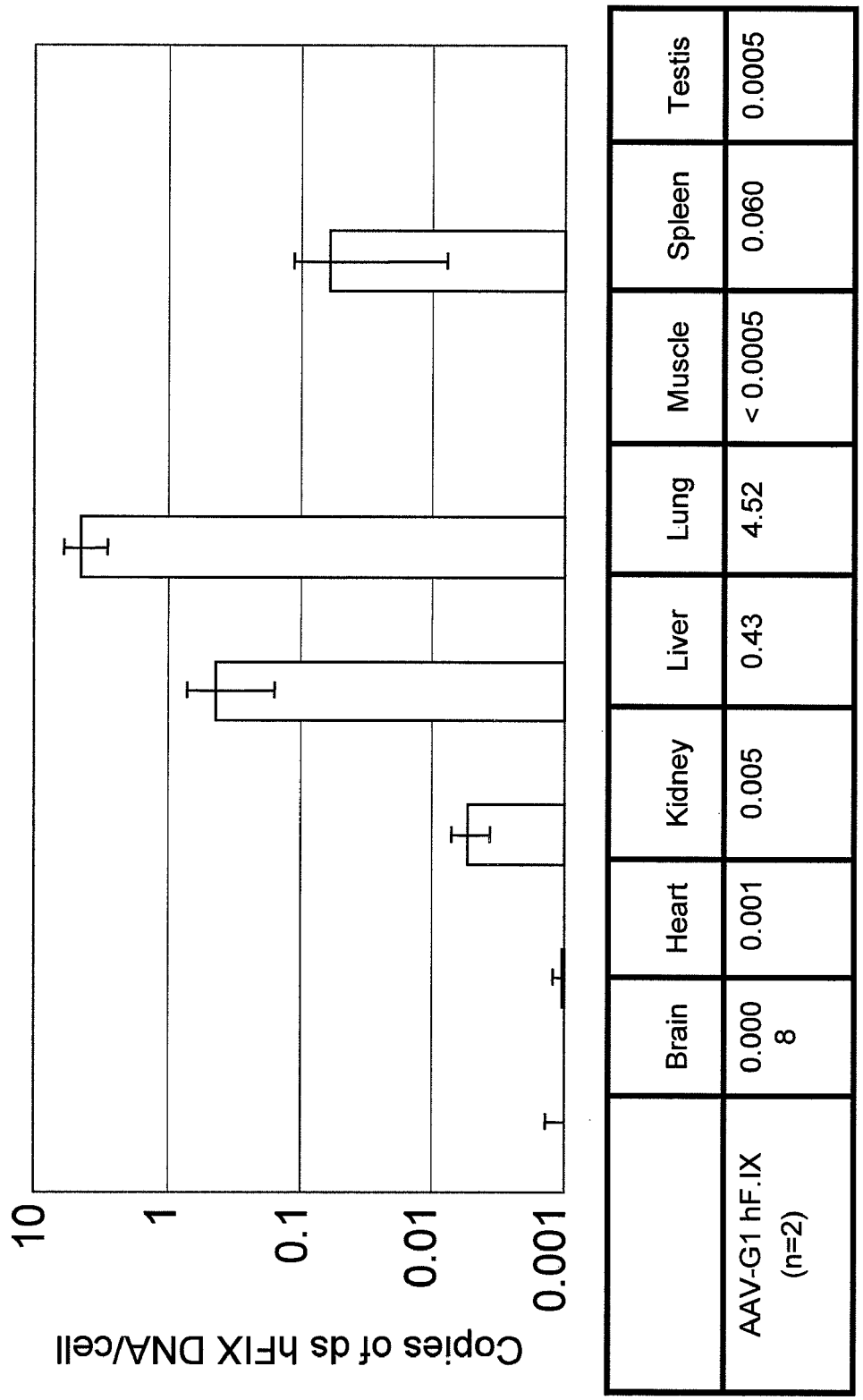
FIG. 4 shows the biodistribution of human factor IX (hFIX) follow intravenous administration of a recombinant caprine AAV vector encoding the same.

As shown in FIG. 4, the biodistribution of IV-administered caprine AAV hF.IX in male SCID mice showed that caprine AAV has lung tropism and is useful for delivering a gene of interest to the lungs of a mammal.

EXAMPLE 3

Isolation of a Bovine AAV

Materials and Methods

Bovine AAV was isolated as follows. Bovine adenovirus (BAV) type 8, strain Misk/67 (available from the ATCC, Manassas, Va., Accession No. VR-769) isolated from calf lungs, was processed for DNA extraction. Virus-containing supernatant was treated with proteinase K (200 µg/ml) in digestion buffer (10 mM Tris-HCl (pH 8.0), 10 mM EDTA (pH 8.0) and 0.5% SDS) and incubated at 37° C. for 1 hour. Following phenol/chloroform extraction and ethanol precipitation, the viral DNA was resuspended in TE.

Oligonucleotide primers for PCR screening were selected on the basis of sequence alignments from segments that are highly conserved among known AAVs.

The forward primer 5'-GTGCCCTTCTACGGCTGCGT-CAACTGGACCAATGAGAAC TTTCC-3' (SEQ ID NO:11) is complementary to the helicase domain of rep and the reverse-primer 5'-GGAATCGCAATGCCAATTTCCT-GAGGCATTAC-3' (SEQ ID NO:12) is complementary to one of the several DNA binding domains in capsid. The expected size of PCR fragments was 1.5 kb.

PCR reaction was performed in 50 µl in an automated Eppendorf Mastercycler®Gradient thermocycler (PerkinElmer, Boston, Mass.). Each reaction mixture contained 200 ng of template DNA, 1 µM each oligonucleotide primer, 1 mM Mn(OAc)$_2$, 200 µM each deoxyribonucleoside triphosphate (dATP, dCTP, dGTP, and dTTP), and 1.0 unit of rTth polymerase, XL (Applied Biosystems, Foster City, Calif.) in 1× XL Buffer II. Ampliwax PCR gem 100 (Applied Biosystems, Foster City, Calif.) was used to facilitate hot start.

Cycling conditions were as follows: 2 min of denaturation at 94° C., followed by 35 cycles of 15 s of denaturation at 94° C., 30 s of annealing at 45° C., and 2 min of elongation at 72° C. PCR products (10 µl) were electrophoretically separated in a 1% NuSieve® agarose gel (FMC BioProducts, Rockland, Minn.), stained with ethidium bromide, and visualized by ultraviolet light. To control for specificity, PCR was also performed with 100 ng of DNA from a plasmid containing AAV-2 rep and cap sequences. PCR products were purified on 1% low-melting agarose gels (FMC Bioproducts, Rockland, Me.) and sequenced using a model 3700HT DNA sequencer (Applied Biosystems, Foster City, Calif.). Sequence data was analyzed with the Vector NTI, version 9.0 package (Invitrogen, San Diego, Calif.).

The plasmid pHLP19-cow was constructed as follows. The AAV-6 capsid gene and 3' untranslated region (UTR) of pHLP19-6 (composed of the AAV-2 rep and the AAV-6 capsid and 3'UTR (Grimm et al. (2003) *Blood* 102:2412-9), were removed by digesting with SwaI and AgeI (New England Biolabs). A bovine capsid coding region tailed with an AAV-6 3' UTR sequence was created by PCR using the following set of primers: 5'-AAATCAGGTATGTCTTTTGTTGAT-CACCC-3' (SEQ ID NO:13) and 5'-ACACGAATTAACCG-GTTTATTGAGGGTATGCGACATGAATGGG-3' (SEQ ID NO:14). The PCR fragment was digested with AgeI and ligated to the digested pHLP19-6 plasmid.

Recombinant bovine AAV vectors were produced and purified as follows, using a triple transfection procedure (Matsushita et al. (1998) *Gene Ther* 5:938-45). In each case the adenovirus helper gene plasmid pLadeno5 and the appropriate AAV helper plasmid (e.g., pHLP19-cow) were used. The transgene plasmids were pVmLacZ (to express lacZ under CMV promoter control), pAAV hFIX9 (to express human factor IX under the CMV promoter control) (Miao et al. (2003) *Hum Gene Ther* 14:1297-305).

Human embryonic kidney cells type 293 (ATCC, catalog number CRL-1573) were transfected, and after six hours the DNA mixture was removed from the cells, which were then provided with fresh cell culture medium without fetal calf serum and the cells were incubated for a 66 hour production period. Then the cells were collected, disrupted, and vector was purified by polyethylene glycol precipitation followed by two rounds of CsCl density gradient centrifugation as described previously (Grimm et al. (2003) Blood 102:2412-9). The purified vector was formulated in PBS, 0.01% Pluronic F-68 and sterile filtered (0.22 µM).

Vector genome titers were established by taking the average of three Q-PCR determinations (Heid et al. (1996) Genome Res 6:986-94) using primers and probe specific for hFIX as previously described (Sommer et al. (2003) Mol Ther 7:122-8).

Viral purity was assessed by SDS-PAGE (Invitrogen, Carlsbad, Calif.) and silver staining (Daiichi, Tokyo, Japan). Monodispersity was assessed by dynamic light scattering using a Protein Solutions, DynaPro® model according to the manufacturer's recommendations (Charlottesville, Va., USA). Analysis of $1 \times 10^{12}$ to $1 \times 10^{11}$ particles in a volume of 12 µl showed hydrodynamic radii of 12 nm for 100% of the vectors in each preparation used for the in vivo studies (bovine AAV hFIX9, AAV-8 hFIX9), indicating that the particles were monomeric and not aggregated.

Analysis

Bovine AAV was partially amplified by PCR, and sequenced. FIG. 5 shows the amino acid sequence of VP1 from the bovine AAV isolated here (SEQ ID NO:5) and the previously described bovine AAV (Schmidt et al. (2004) J Virol 78:6509-16) (SEQ ID NO:6), referred to herein as "Schmidt et al. bovine AAV." In particular, Schmidt et al. bovine AAV was partially amplified from bovine adenovirus type 2. Comparison of the nucleotide sequence of VP1 from bovine AAV and Schmidt et al. bovine AAV showed 12 nucleotide changes 5 amino acid differences. These differences occurred at positions 334 (Q substituted for H), 464 (K substituted for N), 465 (T substituted for K), 499 (R substituted for G) and 514 (G substituted for R). See FIG. 5.

VP1 from bovine AAV displayed 76% identity with AAV-4. Bovine AAV displayed 54% identity with AAV-5 VP1, with high homology in the Rep protein, the first 137 amino acids of AAV-5 VP1 and the non translated region after the stop of AAV-5 VP1 (not shown). Thus, bovine AAV appears to be a natural hybrid between AAV-5 and AAV-4. Bovine AAV also displayed approximately 58% sequence identity with VP1s from AAV-2 and AAV-8, approximately 59% sequence identity with VP1s from AAV-1 and AAV-6, and approximately 60% sequence identity with VP1 from AAV-3B.

The sequence differences between AAV-4 and bovine AAV were scattered throughout the capsid. The similarity with the AAV-4 sequence was from the VP2 start to the capsid stop. Bovine AAV appears to be one of the most divergent of the mammalian AAVs with approximately 58% sequence homology with AAV-2.

The full capsid of bovine AAV was cloned in a plasmid that was used for triple transfection procedure to pseudotyped AAV-2 vector genomes. A bovine AAV vector containing the lacZ gene (bovine AAV lacZ) was produced for further characterization, using the techniques described above. Bovine AAV lacZ vector was produced efficiently; high titers of vector ($1.23 \times 10^{12}$ vg/mL) were detected by Q-PCR. Bovine AAV lacZ vector showed efficient transduction of cells in vitro (cells expressing lacZ were present in numbers comparable to other AAVs).

EXAMPLE 4

Immunoreactivity of a Bovine AAV

In vitro neutralization assays were performed as follows. Human Intravenous Immune Globulin (IVIG; Panglobulin, ZLB Bioplasma Inc. Glendale, Calif.) was resuspended at a concentration of 100 mg/mL and then serially diluted in 2-fold increments using mouse serum (Nieffenegger Company, Woodland, Calif.) filter sterilized, heated at 56° C. for 30 min. Virus was diluted to $2.5 \times 10^9$ vg/µL using EMEM/0.1% Bovine Serum Albumin (BSA, Fraction V, Sigma). All neutralization reactions were performed in triplicate. Samples of EMEM/0.1% BSA and mouse serum alone were included as controls. Ten microliters of diluted AAV lacZ vector were mixed with 10 µl of serial dilutions of the IVIG and incubated at 37° C. for one hour. During the incubation, the HepG2 cells (ATCC catalog #HB-8065) were washed once with EMEM and then 0.5 mL of EMEM/0.1% BSA was added to each well. The amount of vector/IVIG mixture added to the cells for each vector was based on their transduction efficiency, dilutions of the mixture were prepared for the vectors with higher transduction efficiency in order to have equivalent number of blue cells when reading the plates transduced with different vectors. After one hour incubation at 37° C., FBS and etoposide was added to each well at a final concentration of 10% and 20 µM respectively. Cells were incubated for 24 hours, fixed as described above to detect β-galactosidase activity. After another 24 hours, the number of blue cells in each well were counted using light microscopy. The lowest concentration of IVIG tested showing 50% of neutralization was determined.

Bovine AAV relative was 27 times more resistant to neutralization by human IVIG than primate AAV-2 in vitro. The concentration of IVIG (mg/mL) showing 50% neutralization of AAV-2 was 0.7 mg/mL while AAV-8 was 9 mg/mL and bovine AAV was 19 mg/mL.

EXAMPLE 5

Lung Tropism of Bovine AAV

A. In Vivo Transduction of Muscle

Male SCID mice (15-25 g, 6 weeks old) were injected with bovine AAV hFIX9 ($2 \times 10^{11}$ vector genomes per mouse, 5 mice per group), into two sites of the quadriceps muscle (25 µl per site). Retro-orbital blood was collected at seven-day intervals after vector injection and circulating plasma concentrations of hFIX were measured by ELISA (FIX-EIA, Affinity Biologicals). All samples are assessed in duplicate. The lowest limit of detection is 0.02 ng/mL hFIX.

Results are presented at FIGS. 6A and 6B. Low levels of hFIX were observed in the plasma of the mice injected with the bovine AAV hFIX9 vector ("CO" in FIG. 6A), suggesting that the recombinant bovine AAV vector does not efficiently transduce muscle. FIG. 6A. High levels of expression were observed after administration of AAV-8 hFIX9 and AAV-1 hFIX9 vectors (FIG. 6B), consistent with the results observed previously by others (Gao et al. (2002) Proc Natl Acad Sci USA 99:11854-9; Grimm et al. (2003) Blood 102:2412-9).

B. In Vivo Transduction after Tail Vein Delivery

Male SCID mice (15-25 g) were injected via the tail vein with $5 \times 10^{11}$ vector genomes of bovine AAV hFIX-9 or AAV-8 hFIX-9 vectors (5 mice per group). Retro-orbital blood was collected 1, 2, 4 (5 mice per group) and 8 weeks (2 mice per group) after injection and circulating plasma concentrations of human factor IX were measured by ELISA (Walter et al. (1996) Proc Natl Acad Sci USA 93:3056-61). All samples are assessed in duplicate.

Figure 7:
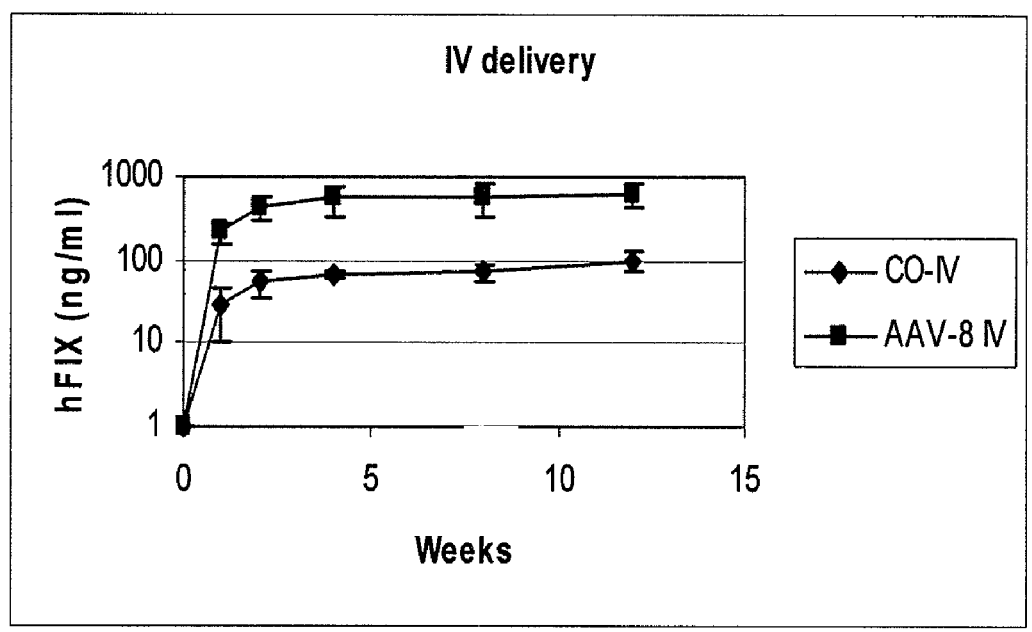
FIG. 7 shows factor IX expression after systemic delivery of bovine AAV and AAV-8 derived factor IX vectors in SCID mice. Male SCID mice were injected via the tail vein with $5 \times 10^{11}$ vector genomes of bovine rAAV hFIX9 (◆) or rAAV-8 hFIX9 (■) (n=5). Retro-orbital blood was collected 1, 2, 4 (n=5) and 8 weeks (n=3) after vector injection. Human factor IX was measured by ELISA.

Results are presented at FIG. 7. The bovine AAV hFIX9 vector ("CO IV" in FIG. 7) produced plasma hFIX levels that were approximately 10-fold lower than those produced by the AAV-8 hFIX9 vector. The hFIX expression construct was driven by the CMV promoter and consequently we can not determine what tissue is contributing to the hFIX expression.

C. Biodistribution of Bovine AAV Vector

Figure 8:
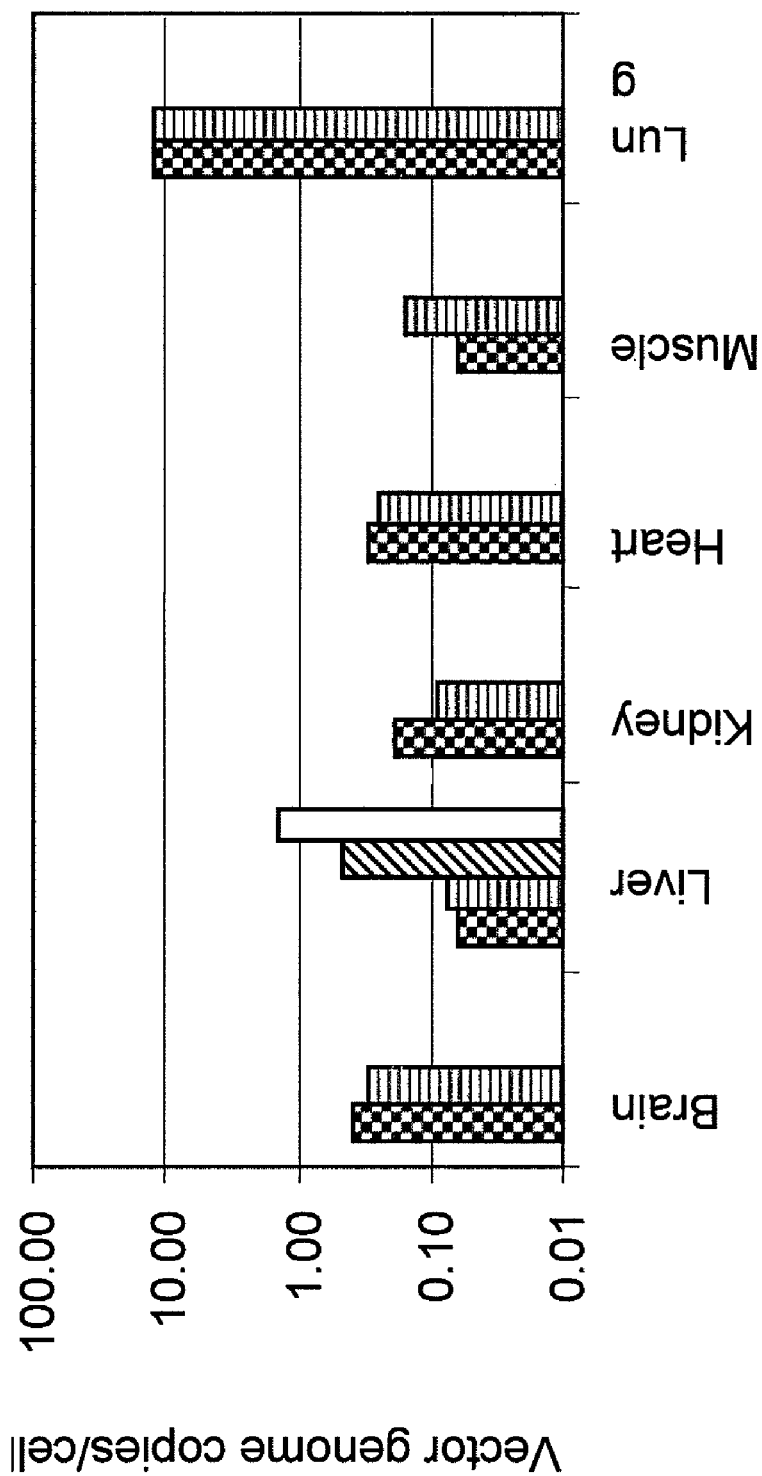
FIG. 8 shows the biodistribution of bovine rAAV hFIX9 after intravenous administration. Human factor IX DNA was quantitated in eight mouse tissues collected 12 weeks after intravenous administration of the recombinant bovine AAV vector. For each vector, tissues from two animals were analyzed and the results for each animal are presented. Bovine AAV hFIX9 (bars with black and white squares and bars with horizontal stripes) AAV-8 hFIX9 (bars in solid black and solid white).

For the biodistribution analysis, mice were sacrificed 12 weeks after IV injection of $5 \times 10^{11}$ vg per mouse. Organs collected included brain, testis, muscle (quadriceps), kidney, brain, lung, muscle (quadriceps), and liver. To measure the copy number of the hFIX gene, quantitative-PCR was done on DNA samples extracted from these tissues. The biodistribution analysis of IV-administered bovine AAV hFIX9 vector in male SCID mice indicated that the bovine AAV had a pronounced lung tropism, as illustrated in FIG. 8.

D. Expression in Lung after Systemic Administration

Whole mount X-gal staining in mouse lung after systemic administration of different AAV serotypes carrying the β-galactosidase transgene was performed as follows. Male SCID mice (15-25 g) were injected via the tail vein with $5 \times 10^{11}$ vector genomes of AAV-4 lacZ, AAV-5 lacZ, AAV-6 lacZ, caprine AAV lacZ, bovine AAV lacZ vectors (5 mice per group). The lung collection method was modified from the previously described (Hofland et al. (1997) *Pharm Res* 14:742-9). Animals received deep isoflurane anesthesia; the trachea was intubated and the lungs inflated with 5 mL of air. Cardiac perfusion with PBS was followed by perfusion with fixative. Lungs were postfixed by immersion in the same fixative for 30 min, in addition the lungs were flushed via the intubation tube. Washes with PBS containing 2 mM $MgCl_2$; were repeated it 3 times for 5 min. The lungs were then incubated with the Xgal substrate solution at 37° C. overnight. The lungs were washed again as described above. The tissues were equilibrated in 30% sucrose solution and pictures of the whole lungs were taken followed by OCT embedding. 7-12 μm thick frozen sections were counter-stained with nuclear fast red.

The results demonstrate that bovine AAV is the most efficient vector transducing the lungs. The results also demonstrate that the staining is localized mainly to the epithelial cells of the bronchioles. A total of 31 bronchioles were counted on two slides and seven of these were positive. These cells are an important target for the treatment of cystic fibrosis since the presence of the CFTR was reported in the literature (Goncz et al. (2001) *Gene Ther* 8:961-5, Wilson (1995) *J Clin Invest* 96:2547-54). Previous reports compared the efficacy of AAV vectors for the transduction of the lung (Auricchio et al. (2002) *J Clin Invest* 110:499-504; Bals et al. (1999) *J Virol* 73:6085-8; Beck et al. (1999) *Virol* 73:9446-55; Fischer et al. (2003) *Mol Ther* 8:918-26; Flotte et al. (2003) *Hum Gene Ther* 14:1079-88; Halbert et al. (2001) *J Virol* 75:6615-24; Halbert et al. (2000) *J Virol* 74:1524-32), but in previous studies the AAVs were delivered through the airway. Here we report the use of a bovine AAV which has lung tropism after systemic administration.

Thus, methods for making and using caprine and bovine rAAV virions with lung tropism are described. Although preferred embodiments of the subject invention have been described in some detail, it is understood that obvious variations can be made without departing from the spirit and the scope of the invention as defined herein.

We claim:

1. A method of providing a protein to the lung of a vertebrate subject, said method comprising:
   (a) providing an infectious recombinant AAV virion which comprises an AAV vector comprising a heterologous nucleic acid molecule encoding the protein operably linked to control elements capable of directing the in vivo expression of said protein, wherein the nucleic acid molecule is flanked on each end with an AAV inverted terminal repeat, wherein the AAV vector is encapsidated by a viral capsid comprising caprine VP1; and
   (b) administering said recombinant AAV virion to said vertebrate subject, wherein said administration results in delivery of the virion to the lung and said protein is expressed in the lung.

2. The method of claim 1, wherein the protein is selected from the group consisting of CFTR, alpha-1-antitrypsin, superoxide dismutase (SOD), interleukin-1, interleukin-2, interleukin-3, interleukin-4, gamma-interferon, p53, and the retinoblastoma gene product.

3. The method of claim 2, wherein the protein is CFTR.

4. The method of claim 1, wherein said administering is to the vasculature of the subject.

5. The method of claim 4, wherein said administering is by intravenous injection.

6. The method of claim 1, wherein the recombinant AAV virions exhibit a tropism for lung tissue resulting in more viral genomes per cell in lung than in any other tissue.

7. The method of claim 1, wherein the caprine VP1 comprises the amino acid sequence of SEQ ID NO:4.

* * * * *